(12) United States Patent
Kalos et al.

(10) Patent No.: US 11,203,640 B2
(45) Date of Patent: Dec. 21, 2021

(54) CHECKPOINT INHIBITOR BISPECIFIC ANTIBODIES

(71) Applicants: Eli Lilly and Company, Indianapolis, IN (US); Zymeworks Inc., Vancouver (CA)

(72) Inventors: Michael Dewain Kalos, Brooklyn, NY (US); Yiwen Li, Woodcliff Lake, NJ (US); Dale Lincoln Ludwig, Rockaway, NJ (US); Yang Shen, Scarsdale, NJ (US); Igor Edmondo Paolo D'Angelo, Anmore (CA); Gregory D Plowman, New York, NY (US)

(73) Assignees: Eli Lilly and Company, Indianapolis, IN (US); Zymeworks Inc., Vancouver (CA)

( * ) Notice: Subject to any disclaimer, the term of this patent is extended or adjusted under 35 U.S.C. 154(b) by 686 days.

(21) Appl. No.: 16/029,979

(22) Filed: Jul. 9, 2018

(65) Prior Publication Data

US 2019/0010232 A1 Jan. 10, 2019

Related U.S. Application Data

(60) Provisional application No. 62/530,436, filed on Jul. 10, 2017.

(51) Int. Cl.
| | | |
|---|---|---|
| *C07K 16/28* | (2006.01) | |
| *A61P 35/00* | (2006.01) | |
| *A61K 39/395* | (2006.01) | |
| *A61K 45/06* | (2006.01) | |
| *C07K 16/46* | (2006.01) | |
| *A61K 39/00* | (2006.01) | |

(52) U.S. Cl.
CPC .... *C07K 16/2818* (2013.01); *A61K 39/39558* (2013.01); *A61K 45/06* (2013.01); *A61P 35/00* (2018.01); *C07K 16/2827* (2013.01); *C07K 16/468* (2013.01); *A61K 2039/505* (2013.01); *C07K 2317/24* (2013.01); *C07K 2317/31* (2013.01); *C07K 2317/51* (2013.01); *C07K 2317/515* (2013.01); *C07K 2317/524* (2013.01); *C07K 2317/64* (2013.01)

(58) Field of Classification Search
None
See application file for complete search history.

(56) References Cited

U.S. PATENT DOCUMENTS

| 9,248,181 B2 | 2/2016 | De Kruif et al. |
|---|---|---|
| 2015/0210769 A1 | 7/2015 | Freeman et al. |
| 2017/0044260 A1 | 2/2017 | Baruah et al. |
| 2017/0058033 A1 | 3/2017 | Ludwig et al. |

FOREIGN PATENT DOCUMENTS

| WO | 2011120134 A1 | 10/2011 |
|---|---|---|
| WO | 2012037659 A1 | 3/2012 |
| WO | 2012040833 A1 | 4/2012 |
| WO | 2012058768 A1 | 5/2012 |
| WO | 2012116453 A1 | 9/2012 |
| WO | 2013063702 A1 | 5/2013 |
| WO | 2013166594 A1 | 11/2013 |
| WO | 2013166604 A1 | 11/2013 |
| WO | 2014012082 A2 | 1/2014 |
| WO | 2014012085 A2 | 1/2014 |
| WO | 2014018572 A1 | 1/2014 |
| WO | 2014055784 A1 | 4/2014 |
| WO | 2014067011 A1 | 5/2014 |
| WO | 2014082179 A1 | 6/2014 |
| WO | 2015109131 A2 | 7/2015 |
| WO | 2015181805 A1 | 12/2015 |
| WO | 2016/061142 | 4/2016 |
| WO | 2017/017623 | 2/2017 |
| WO | 2017087547 A1 | 5/2017 |

OTHER PUBLICATIONS

Pitt et al (I, 44:1255-1269, 2016).*
Stanciu et al (JID, 193:404-412, 2005).*
Liu et al (AB, 117:361-373, 2020).*
International Search Report for PCT/US2018/041205.
Written Opinion for PCT/US2018/041205.
ClinicalTrials.gov[Internet]. Bethesda (MD): National Library of Medicine (US). Oct. 18, 2016—Identifier NCT02936102, "A Study of FAZ053 Single Agent and in Combination With PDR001 in Patients With Advanced Malignancies." Available from: https://www.clinicaltrials.gov/ct2/show/NCT02936102?term=PDR001+and+FAZ053&rank=1.
ClinicalTrials.gov[Internet]. Bethesda (MD): National Library of Medicine (US). Apr. 21, 2014—Identifier NCT02118337, "Open-label Study to Evaluate the Safety and Antitumor Activity of MEDI0680 (AMP-514) in Combination With Durvalumab Versus Nivolumab Monotherapy in Subjects With Select Advanced Malignancies." Available from: https://www.clinicaltrials.gov/ct2/show/NCT02118337?term=MEDI0680+and+durvalmab&rank=1.
Hamid, et al., "Combination of MEDI0680, an anti-PD-1 antibody, with durvalumab, an anti-PD-L1 antibody: A phase 1, open-label study in advanced malignancies," Annals of Oncology, vol. 27, Supplement 6, pp. vi359-vi378 (2016).
Sharma, et al., "Immune Chekcpoint Targeting in Cancer Therapy: Toward Combination Strategies with Curative Potential," Cell, vol. 161, 205-214 (2015).
Kreudenstein, et al., "Protein engineering and the use of molecular modeling and simulation: The case of heterodimeric Fc engineering," Methods, vol. 65, pp. 77-94 (2014).

(Continued)

*Primary Examiner* — Brad Duffy
(74) *Attorney, Agent, or Firm* — Grant E. Reed

(57) ABSTRACT

The present invention relates to antibodies that are heterodimeric and bind human PD-L1 and human PD-1, and may be useful for treating cancer alone and in combination with chemotherapy and other cancer therapeutics.

5 Claims, No Drawings
Specification includes a Sequence Listing.

(56) References Cited

OTHER PUBLICATIONS

Kreudenstein, et al., "Improving biophysical properties of a bispecific antibody scaffold to aid developability," mAbs, vol. 5, No. 5, pp. 646-654 (2013).

Woods, et al., "LC-MS characterization and purity assessment of a prototype bispecific antibody," mAbs, vol. 5, No. 5, pp. 711-722 (2013).

PCT Application No. PCT/US18/26060 filed Apr. 4, 2018 by Eli Lilly and Company.

* cited by examiner

SEQUENCE LISTING

<160> NUMBER OF SEQ ID NOS: 51

<210> SEQ ID NO 1
<211> LENGTH: 290
<212> TYPE: PRT
<213> ORGANISM: Homo sapiens

<400> SEQUENCE: 1

```
Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160
```

-continued

```
Pro Lys Ala Glu Val Ile Trp Thr Ser Ser Asp His Gln Val Leu Ser
            165                 170                 175
Gly Lys Thr Thr Thr Thr Asn Ser Lys Arg Glu Glu Lys Leu Phe Asn
        180                 185                 190
Val Thr Ser Thr Leu Arg Ile Asn Thr Thr Thr Asn Glu Ile Phe Tyr
        195                 200                 205
Cys Thr Phe Arg Arg Leu Asp Pro Glu Glu Asn His Thr Ala Glu Leu
    210                 215                 220
Val Ile Pro Glu Leu Pro Leu Ala His Pro Pro Asn Glu Arg Thr His
225                 230                 235                 240
Leu Val Ile Leu Gly Ala Ile Leu Leu Cys Leu Gly Val Ala Leu Thr
                245                 250                 255
Phe Ile Phe Arg Leu Arg Lys Gly Arg Met Met Asp Val Lys Lys Cys
            260                 265                 270
Gly Ile Gln Asp Thr Asn Ser Lys Lys Gln Ser Asp Thr His Leu Glu
        275                 280                 285
Glu Thr
    290
```

<210> SEQ ID NO 2
<211> LENGTH: 288
<212> TYPE: PRT
<213> ORGANISM: Homo sapiens

<400> SEQUENCE: 2

```
Met Gln Ile Pro Gln Ala Pro Trp Pro Val Val Trp Ala Val Leu Gln
1               5                   10                  15
Leu Gly Trp Arg Pro Gly Trp Phe Leu Asp Ser Pro Asp Arg Pro Trp
            20                  25                  30
Asn Pro Pro Thr Phe Ser Pro Ala Leu Leu Val Val Thr Glu Gly Asp
        35                  40                  45
Asn Ala Thr Phe Thr Cys Ser Phe Ser Asn Thr Ser Glu Ser Phe Val
    50                  55                  60
Leu Asn Trp Tyr Arg Met Ser Pro Ser Asn Gln Thr Asp Lys Leu Ala
65                  70                  75                  80
Ala Phe Pro Glu Asp Arg Ser Gln Pro Gly Gln Asp Cys Arg Phe Arg
                85                  90                  95
Val Thr Gln Leu Pro Asn Gly Arg Asp Phe His Met Ser Val Val Arg
            100                 105                 110
Ala Arg Arg Asn Asp Ser Gly Thr Tyr Leu Cys Gly Ala Ile Ser Leu
        115                 120                 125
Ala Pro Lys Ala Gln Ile Lys Glu Ser Leu Arg Ala Glu Leu Arg Val
    130                 135                 140
Thr Glu Arg Arg Ala Glu Val Pro Thr Ala His Pro Ser Pro Ser Pro
145                 150                 155                 160
Arg Pro Ala Gly Gln Phe Gln Thr Leu Val Val Gly Val Val Gly Gly
                165                 170                 175
Leu Leu Gly Ser Leu Val Leu Leu Val Trp Val Leu Ala Val Ile Cys
            180                 185                 190
Ser Arg Ala Ala Arg Gly Thr Ile Gly Ala Arg Arg Thr Gly Gln Pro
        195                 200                 205
Leu Lys Glu Asp Pro Ser Ala Val Pro Val Phe Ser Val Asp Tyr Gly
    210                 215                 220
Glu Leu Asp Phe Gln Trp Arg Glu Lys Thr Pro Glu Pro Pro Val Pro
225                 230                 235                 240
```

```
Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285

<210> SEQ ID NO 3
<211> LENGTH: 123
<212> TYPE: PRT
<213> ORGANISM: Artificial Sequence
<220> FEATURE:
<223> OTHER INFORMATION: Synthetic construct

<400> SEQUENCE: 3

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Pro Asp Tyr Ser Pro Tyr Tyr Tyr Gly Met Asp Val
            100                 105                 110

Trp Gly Gln Gly Thr Thr Val Thr Val Ser Ser
        115                 120

<210> SEQ ID NO 4
<211> LENGTH: 111
<212> TYPE: PRT
<213> ORGANISM: Artificial Sequence
<220> FEATURE:
<223> OTHER INFORMATION: Synthetic construct

<400> SEQUENCE: 4

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Gly Asn Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Gln Ser Tyr Asp Ser Ser Leu
                85                  90                  95

Ser Gly Ser Val Phe Gly Gly Gly Ile Lys Leu Thr Val Leu Gly
            100                 105                 110

<210> SEQ ID NO 5
<211> LENGTH: 120
<212> TYPE: PRT
```

<213> ORGANISM: Artificial Sequence
<220> FEATURE:
<223> OTHER INFORMATION: Synthetic construct
<220> FEATURE:
<221> NAME/KEY: Xaa
<222> LOCATION: (54)..(54)
<223> OTHER INFORMATION: Xaa = M or S

<400> SEQUENCE: 5

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Leu Ile Ile Pro Xaa Phe Asp Thr Ala Gly Tyr Ala Gln Lys Phe
    50                  55                  60

Gln Gly Arg Val Ala Ile Thr Val Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Glu His Ser Ser Thr Gly Thr Phe Asp Tyr Trp Gly Gln
            100                 105                 110

Gly Thr Leu Val Thr Val Ser Ser
        115                 120

<210> SEQ ID NO 6
<211> LENGTH: 120
<212> TYPE: PRT
<213> ORGANISM: Artificial Sequence
<220> FEATURE:
<223> OTHER INFORMATION: Synthetic construct

<400> SEQUENCE: 6

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Leu Ile Ile Pro Ser Phe Asp Thr Ala Gly Tyr Ala Gln Lys Phe
    50                  55                  60

Gln Gly Arg Val Ala Ile Thr Val Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Glu His Ser Ser Thr Gly Thr Phe Asp Tyr Trp Gly Gln
            100                 105                 110

Gly Thr Leu Val Thr Val Ser Ser
        115                 120

<210> SEQ ID NO 7
<211> LENGTH: 120
<212> TYPE: PRT
<213> ORGANISM: Artificial Sequence
<220> FEATURE:
<223> OTHER INFORMATION: Synthetic construct

<400> SEQUENCE: 7

Gln Val Gln Leu Val Gln Ser Gly Ala Glu Val Lys Lys Pro Gly Ser

```
                1               5                   10                  15
Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
                35                  40                  45

Gly Leu Ile Ile Pro Met Phe Asp Thr Ala Gly Tyr Ala Gln Lys Phe
            50                  55                  60

Gln Gly Arg Val Ala Ile Thr Val Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Glu His Ser Ser Thr Gly Thr Phe Asp Tyr Trp Gly Gln
                100                 105                 110

Gly Thr Leu Val Thr Val Ser Ser
            115                 120
```

<210> SEQ ID NO 8
<211> LENGTH: 107
<212> TYPE: PRT
<213> ORGANISM: Artificial Sequence
<220> FEATURE:
<223> OTHER INFORMATION: Synthetic construct

<400> SEQUENCE: 8

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
                20                  25                  30

Leu Ala Trp Tyr Gln Gln Lys Pro Gly Lys Ala Pro Lys Leu Leu Ile
                35                  40                  45

Ser Ala Ala Ser Ser Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn His Leu Pro Phe
                85                  90                  95

Thr Phe Gly Gly Gly Thr Lys Val Glu Ile Lys
                100                 105
```

<210> SEQ ID NO 9
<211> LENGTH: 5
<212> TYPE: PRT
<213> ORGANISM: Artificial Sequence
<220> FEATURE:
<223> OTHER INFORMATION: Synthetic construct

<400> SEQUENCE: 9

```
Ser Leu Lys Ser Val
1               5
```

<210> SEQ ID NO 10
<211> LENGTH: 32
<212> TYPE: PRT
<213> ORGANISM: Artificial Sequence
<220> FEATURE:
<223> OTHER INFORMATION: Synthetic construct

<400> SEQUENCE: 10

```
Ala Ala Gly Gly Pro Ser Val Phe Leu Phe Pro Pro Lys Pro Lys Asp
1               5                   10                  15
```

```
Thr Leu Met Ile Ser Arg Thr Pro Glu Val Thr Cys Val Val Val Ser
        20                  25                  30
```

<210> SEQ ID NO 11
<211> LENGTH: 58
<212> TYPE: PRT
<213> ORGANISM: Artificial Sequence
<220> FEATURE:
<223> OTHER INFORMATION: Synthetic construct

<400> SEQUENCE: 11

```
Val Tyr Pro Pro Ser Arg Asp Glu Leu Thr Lys Asn Gln Val Ser Leu
1               5                   10                  15

Thr Cys Leu Val Lys Gly Phe Tyr Pro Ser Asp Ile Ala Val Glu Trp
            20                  25                  30

Glu Ser Asn Gly Gln Pro Glu Asn Asn Tyr Lys Thr Thr Pro Pro Val
        35                  40                  45

Leu Asp Ser Asp Gly Ser Phe Ala Leu Val
    50                  55
```

<210> SEQ ID NO 12
<211> LENGTH: 45
<212> TYPE: PRT
<213> ORGANISM: Artificial Sequence
<220> FEATURE:
<223> OTHER INFORMATION: Synthetic construct

<400> SEQUENCE: 12

```
Val Leu Pro Pro Ser Arg Asp Glu Leu Thr Lys Asn Gln Val Ser Leu
1               5                   10                  15

Leu Cys Leu Val Lys Gly Phe Tyr Pro Ser Asp Ile Ala Val Glu Trp
            20                  25                  30

Glu Ser Asn Gly Gln Pro Glu Asn Asn Tyr Leu Thr Trp
        35                  40                  45
```

<210> SEQ ID NO 13
<211> LENGTH: 48
<212> TYPE: PRT
<213> ORGANISM: Artificial Sequence
<220> FEATURE:
<223> OTHER INFORMATION: Synthetic construct

<400> SEQUENCE: 13

```
Glu Ala Pro Ser Ser Lys Ser Thr Ser Gly Gly Thr Ala Ala Leu Gly
1               5                   10                  15

Cys Leu Val Thr Asp Tyr Phe Pro Glu Pro Val Thr Val Ser Trp Asn
            20                  25                  30

Ser Gly Ala Leu Thr Ser Gly Val His Thr Phe Pro Ala Val Leu Glu
        35                  40                  45
```

<210> SEQ ID NO 14
<211> LENGTH: 7
<212> TYPE: PRT
<213> ORGANISM: Artificial Sequence
<220> FEATURE:
<223> OTHER INFORMATION: Synthetic construct

<400> SEQUENCE: 14

```
Ala Ala Glu Ser Glu Leu Ser
1               5
```

<210> SEQ ID NO 15

<211> LENGTH: 46
<212> TYPE: PRT
<213> ORGANISM: Artificial Sequence
<220> FEATURE:
<223> OTHER INFORMATION: Synthetic construct

<400> SEQUENCE: 15

Arg Val Gly Cys Leu Leu Asn Asn Phe Tyr Pro Arg Glu Ala Lys Val
1               5                   10                  15

Gln Trp Lys Val Asp Asn Ala Leu Gln Ser Gly Asn Ser Gln Glu Ser
            20                  25                  30

Val Thr Glu Gln Asp Ser Lys Asp Ser Thr Tyr Ser Leu Arg
        35                  40                  45

<210> SEQ ID NO 16
<211> LENGTH: 13
<212> TYPE: PRT
<213> ORGANISM: Artificial Sequence
<220> FEATURE:
<223> OTHER INFORMATION: Synthetic construct

<400> SEQUENCE: 16

Lys Ala Ser Gly Gly Thr Phe Ser Ser Tyr Ala Ile Ser
1               5                   10

<210> SEQ ID NO 17
<211> LENGTH: 17
<212> TYPE: PRT
<213> ORGANISM: Artificial Sequence
<220> FEATURE:
<223> OTHER INFORMATION: Synthetic construct

<400> SEQUENCE: 17

Gly Ile Ile Pro Ile Phe Gly Thr Ala Asn Tyr Ala Gln Lys Phe Gln
1               5                   10                  15

Gly

<210> SEQ ID NO 18
<211> LENGTH: 16
<212> TYPE: PRT
<213> ORGANISM: Artificial Sequence
<220> FEATURE:
<223> OTHER INFORMATION: Synthetic construct

<400> SEQUENCE: 18

Ala Arg Ser Pro Asp Tyr Ser Pro Tyr Tyr Tyr Tyr Gly Met Asp Val
1               5                   10                  15

<210> SEQ ID NO 19
<211> LENGTH: 13
<212> TYPE: PRT
<213> ORGANISM: Artificial Sequence
<220> FEATURE:
<223> OTHER INFORMATION: Synthetic construct

<400> SEQUENCE: 19

Ser Gly Ser Ser Ser Asn Ile Gly Ser Asn Thr Val Asn
1               5                   10

<210> SEQ ID NO 20
<211> LENGTH: 8
<212> TYPE: PRT
<213> ORGANISM: Artificial Sequence
<220> FEATURE:
<223> OTHER INFORMATION: Synthetic construct

```
<400> SEQUENCE: 20

Tyr Gly Asn Ser Asn Arg Pro Ser
1               5

<210> SEQ ID NO 21
<211> LENGTH: 11
<212> TYPE: PRT
<213> ORGANISM: Artificial Sequence
<220> FEATURE:
<223> OTHER INFORMATION: Synthetic construct

<400> SEQUENCE: 21

Gln Ser Tyr Asp Ser Ser Leu Ser Gly Ser Val
1               5                   10

<210> SEQ ID NO 22
<211> LENGTH: 13
<212> TYPE: PRT
<213> ORGANISM: Artificial Sequence
<220> FEATURE:
<223> OTHER INFORMATION: Synthetic construct

<400> SEQUENCE: 22

Lys Ala Ser Gly Gly Thr Phe Ser Ser Tyr Ala Ile Ser
1               5                   10

<210> SEQ ID NO 23
<211> LENGTH: 17
<212> TYPE: PRT
<213> ORGANISM: Artificial Sequence
<220> FEATURE:
<223> OTHER INFORMATION: Synthetic construct

<400> SEQUENCE: 23

Leu Ile Ile Pro Ser Phe Asp Thr Ala Gly Tyr Ala Gln Lys Phe Gln
1               5                   10                  15

Gly

<210> SEQ ID NO 24
<211> LENGTH: 17
<212> TYPE: PRT
<213> ORGANISM: Artificial Sequence
<220> FEATURE:
<223> OTHER INFORMATION: Synthetic construct

<400> SEQUENCE: 24

Leu Ile Ile Pro Met Phe Asp Thr Ala Gly Tyr Ala Gln Lys Phe Gln
1               5                   10                  15

Gly

<210> SEQ ID NO 25
<211> LENGTH: 13
<212> TYPE: PRT
<213> ORGANISM: Artificial Sequence
<220> FEATURE:
<223> OTHER INFORMATION: Synthetic construct

<400> SEQUENCE: 25

Ala Arg Ala Glu His Ser Ser Thr Gly Thr Phe Asp Tyr
1               5                   10

<210> SEQ ID NO 26
<211> LENGTH: 11
<212> TYPE: PRT
<213> ORGANISM: Artificial Sequence
```

```
<220> FEATURE:
<223> OTHER INFORMATION: Synthetic construct

<400> SEQUENCE: 26

Arg Ala Ser Gln Gly Ile Ser Ser Trp Leu Ala
1               5                   10

<210> SEQ ID NO 27
<211> LENGTH: 8
<212> TYPE: PRT
<213> ORGANISM: Artificial Sequence
<220> FEATURE:
<223> OTHER INFORMATION: Synthetic construct

<400> SEQUENCE: 27

Ser Ala Ala Ser Ser Leu Gln Ser
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic construct

<400> SEQUENCE: 28

Gln Gln Ala Asn His Leu Pro Phe Thr
1               5

<210> SEQ ID NO 29
<211> LENGTH: 453
<212> TYPE: PRT
<213> ORGANISM: Artificial Sequence
<220> FEATURE:
<223> OTHER INFORMATION: Synthetic construct

<400> SEQUENCE: 29

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Pro Asp Tyr Ser Pro Tyr Tyr Tyr Gly Met Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190
```

```
Thr Val Pro Ser Ser Leu Gly Thr Gln Thr Tyr Ile Cys Asn Val
            195                 200                 205

Asn His Lys Pro Ser Asn Thr Lys Val Asp Lys Arg Val Glu Pro Lys
210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Ser Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Val Leu Pro Pro Ser Arg Asp Glu Leu Thr Lys Asn Gln
        355                 360                 365

Val Ser Leu Leu Cys Leu Val Lys Gly Phe Tyr Pro Ser Asp Ile Ala
    370                 375                 380

Val Glu Trp Glu Ser Asn Gly Gln Pro Glu Asn Asn Tyr Leu Thr Trp
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 30
<211> LENGTH: 216
<212> TYPE: PRT
<213> ORGANISM: Artificial Sequence
<220> FEATURE:
<223> OTHER INFORMATION: Synthetic construct

<400> SEQUENCE: 30

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Gly Asn Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Gln Ser Tyr Asp Ser Ser Leu
                85                  90                  95
```

```
Ser Gly Ser Val Phe Gly Gly Ile Lys Leu Thr Val Leu Gly Gln
            100                 105                 110

Pro Lys Ala Ala Pro Ser Val Thr Leu Phe Pro Pro Ser Glu Glu
            115                 120                 125

Leu Gln Ala Asn Lys Ala Thr Leu Val Cys Leu Ile Ser Asp Phe Tyr
            130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                    165                 170                 175

Ala Ala Glu Ser Glu Leu Ser Leu Thr Pro Glu Gln Trp Lys Ser His
                    180                 185                 190

Arg Ser Tyr Ser Cys Gln Val Thr His Glu Gly Ser Thr Val Glu Lys
                    195                 200                 205

Thr Val Ala Pro Ala Glu Cys Ser
            210                 215

<210> SEQ ID NO 31
<211> LENGTH: 450
<212> TYPE: PRT
<213> ORGANISM: Artificial Sequence
<220> FEATURE:
<223> OTHER INFORMATION: Synthetic construct

<400> SEQUENCE: 31

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Leu Ile Ile Pro Ser Phe Asp Thr Ala Gly Tyr Ala Gln Lys Phe
        50                  55                  60

Gln Gly Arg Val Ala Ile Thr Val Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Glu His Ser Ser Thr Gly Thr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Glu Ala Pro Ser Ser Lys Ser Thr Ser Gly Gly Thr Ala Ala
    130                 135                 140

Leu Gly Cys Leu Val Thr Asp Tyr Phe Pro Glu Pro Val Thr Val Ser
145                 150                 155                 160

Trp Asn Ser Gly Ala Leu Thr Ser Gly Val His Thr Phe Pro Ala Val
                    165                 170                 175

Leu Glu Ser Ser Gly Leu Tyr Ser Leu Ser Ser Val Val Thr Val Pro
                    180                 185                 190

Ser Ser Ser Leu Gly Thr Gln Thr Tyr Ile Cys Asn Val Asn His Lys
                    195                 200                 205

Pro Ser Asn Thr Lys Val Asp Lys Arg Val Glu Pro Lys Ser Cys Asp
            210                 215                 220

Lys Thr His Thr Cys Pro Pro Cys Pro Ala Pro Glu Ala Ala Gly Gly
225                 230                 235                 240
```

Pro Ser Val Phe Leu Phe Pro Pro Lys Pro Lys Asp Thr Leu Met Ile
            245                 250                 255

Ser Arg Thr Pro Glu Val Thr Cys Val Val Val Ser Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Val Leu Pro Pro Ser Arg Asp Glu Leu Thr Lys Asn Gln Val Ser Leu
            355                 360                 365

Leu Cys Leu Val Lys Gly Phe Tyr Pro Ser Asp Ile Ala Val Glu Trp
            370                 375                 380

Glu Ser Asn Gly Gln Pro Glu Asn Asn Tyr Leu Thr Trp Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 32
<211> LENGTH: 450
<212> TYPE: PRT
<213> ORGANISM: Artificial Sequence
<220> FEATURE:
<223> OTHER INFORMATION: Synthetic construct

<400> SEQUENCE: 32

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Leu Ile Ile Pro Met Phe Asp Thr Ala Gly Tyr Ala Gln Lys Phe
        50                  55                  60

Gln Gly Arg Val Ala Ile Thr Val Asp Glu Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Ala Glu His Ser Ser Thr Gly Thr Phe Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

```
Leu Gly Cys Leu Val Thr Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Glu Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Ser Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Val Leu Pro Pro Ser Arg Asp Glu Leu Thr Lys Asn Gln Val Ser Leu
        355                 360                 365

Leu Cys Leu Val Lys Gly Phe Tyr Pro Ser Asp Ile Ala Val Glu Trp
    370                 375                 380

Glu Ser Asn Gly Gln Pro Glu Asn Asn Tyr Leu Thr Trp Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 33
<211> LENGTH: 450
<212> TYPE: PRT
<213> ORGANISM: Artificial Sequence
<220> FEATURE:
<223> OTHER INFORMATION: Synthetic construct

<400> SEQUENCE: 33

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45
```

```
Gly Leu Ile Ile Pro Met Phe Asp Thr Ala Gly Tyr Ala Gln Lys Phe
 50                  55                  60

Gln Gly Arg Val Ala Ile Thr Val Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ala Glu His Ser Ser Thr Gly Thr Phe Asp Tyr Trp Gly Gln
            100                 105                 110

Gly Thr Leu Val Thr Val Ser Ser Ala Ser Thr Lys Gly Pro Ser Val
            115                 120                 125

Phe Pro Glu Ala Pro Ser Ser Lys Ser Thr Ser Gly Gly Thr Ala Ala
130                 135                 140

Leu Gly Cys Leu Val Thr Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Glu Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Ser Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Val Tyr Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Ala Leu Val Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
450
```

<210> SEQ ID NO 34
<211> LENGTH: 214
<212> TYPE: PRT
<213> ORGANISM: Artificial Sequence
<220> FEATURE:
<223> OTHER INFORMATION: Synthetic construct

<400> SEQUENCE: 34

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Ser Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn His Leu Pro Phe
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Arg Val Gly Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Arg
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 35
<211> LENGTH: 787
<212> TYPE: DNA
<213> ORGANISM: Artificial Sequence
<220> FEATURE:
<223> OTHER INFORMATION: Synthetic construct

<400> SEQUENCE: 35

```
cagtccgtcc tgactcagcc accttccgct agcggtaccc ccggccagag agtgacaatc      60
tcatgctccg gttccagctc taacattggc tctaacactg tcaattggta ccagcagctg     120
ccaggaaccg caccaaagct gctgatctat ggaaactcaa ataggcctag cggggtgcca     180
gaccggttta gcggatctaa aagtgggact tcagcttccc tggcaatttc tggactgcag     240
agtgaggacg aagctgatta ctattgccag tcctacgata gttcactgag cggttccgtg     300
ttcggcggag ggatcaagct gacagtcctg ggccagccca aggtgagttc tagaggatcc     360
atctgggata agcatgctgt tttctgtctg tccctaacat gccctgtgat tatccgcaaa     420
caacacaccc aagggcagaa ctttgttact taaaccacca cctgtttgct ctttcctca      480 ggccgctcct tcgtgactc tgtttccccc ttccagcgag gaactgcagg ccaataaggc     540
```

| | |
|---|---|
| caccctggtg tgcctgatta gcgacttcta tcctggagct gtgacagtcg catggaaggc | 600 |
| cgattctagt ccagtgaaag caggggtcga gaccacaact ccctccaagc agagcaacaa | 660 |
| caagtacgca gccgagtctg aactgagtct gaccccagaa cagtggaagt cccacaggag | 720 |
| ttattcatgc caggtgaccc atgagggctc cacagtggag aagaccgtgg cccctgctga | 780 |
| gtgtagc | 787 |

<210> SEQ ID NO 36
<211> LENGTH: 642
<212> TYPE: DNA
<213> ORGANISM: Artificial Sequence
<220> FEATURE:
<223> OTHER INFORMATION: Synthetic construct

<400> SEQUENCE: 36

| | |
|---|---|
| gacattcaga tgacccagag cccaagcagc gtgagcgcca gcgtcgggga ccgagtgacc | 60 |
| atcacatgca gggccagcca gggtatttct agttggctgg cttggtacca gcagaagcca | 120 |
| ggcaaagcac ccaagctgct gatctccgcc gcttcaagcc tgcagtccgg agtgccctct | 180 |
| cgattctctg gtagtggctc aggaacagac tttactctga ccatttcctc tctgcagcct | 240 |
| gaggatttcg ctacttacta ttgccagcag gcaaaccacc tgccattcac ctttggcgga | 300 |
| gggacaaaag tggagatcaa agaaccgtc gcggcgccca gtgtcttcat ttttcccct | 360 |
| agcgacgaac agctgaagtc tgggacagcc agagtgggct gtctgctgaa caacttctac | 420 |
| cctagagagg ctaaagtgca gtggaaggtc gataacgcac tgcagtccgg aaattctcag | 480 |
| gagagtgtga ctgaacagga ctcaaaagat agcacctatt ccctgagaag cacactgact | 540 |
| ctgagcaagg ccgactacga gaagcataaa gtgtatgctt gtgaagtcac ccaccagggg | 600 |
| ctgagttcac cagtcacaaa atcattcaac agaggggagt gc | 642 |

<210> SEQ ID NO 37
<211> LENGTH: 1359
<212> TYPE: DNA
<213> ORGANISM: Artificial Sequence
<220> FEATURE:
<223> OTHER INFORMATION: Synthetic construct

<400> SEQUENCE: 37

| | |
|---|---|
| caggtccagc tggtgcagag cggagccgaa gtgaagaaac ccggtagcag cgtcaaagtg | 60 |
| tcatgtaaag cctcagggggg aacattctcc agctacgcca tctcctgggt gagacaggct | 120 |
| ccaggacagg gactggagtg gatgggagga atcatcccta tcttcggcac cgccaactac | 180 |
| gctcagaagt ttcagggccg cgtgaccatc acagccgaca agagcacctc tacagcttat | 240 |
| atggagctgt cttccctgag aagcgaggat acagccgtgt actattgcgc tcgctccccc | 300 |
| gactacagcc ttactatta ctatggcatg gacgtgtggg gccagggcac cacagtgacc | 360 |
| gtgagctctg ctagcacaaa gggcccatcc gtgttcccac tggctccatc cagcaagtcc | 420 |
| accagcggag aacagccgc tctgggctgt ctggtgaagg actatttccc agagccagtg | 480 |
| accgtgtcct ggaacagcgg cgccctgacc tctggagtgc acacattcc cgctgtgctg | 540 |
| cagtcttccg gcctgtactc tctgaagtcc gtggtgaccg tgcctagctc ttccctgggc | 600 |
| acccagacat atatctgcaa cgtgaatcac aagccttcca atacaaaggt ggacaagagg | 660 |
| gtggagccaa agagctgtga taagacccat acatgccccc cttgtcctgc tccagaggct | 720 |
| gctggaggac caagcgtgtt cctgtttcca cccaagccca aggacaccct gatgatctct | 780 |

| | |
|---|---|
| aggaccoctg aggtgacatg cgtggtggtg tccgtgtccc acgaggaccc agaggtgaag | 840 |
| tttaactggt acgtggatgg cgtggaggtg cataatgcta agaccaagcc tagggaggag | 900 |
| cagtacaaca gcacctatcg ggtggtgtct gtgctgacag tgctgcatca ggattggctg | 960 |
| aacggcaagg agtataagtg caaggtgtct aataaggccc tgcccgctcc tatcgagaag | 1020 |
| accatctcca aggccaaggg ccagcctagg gagccacagg tgtacgtgct gcctccaagc | 1080 |
| cgggacgagc tgacaaagaa ccaggtgtct ctgctgtgcc tggtgaaggg cttctatcca | 1140 |
| tctgatatcg ctgtggagtg ggagtccaat ggccagcccg agaacaatta cctgacctgg | 1200 |
| cccccctgtgc tggacagcga tggctctttc tttctgtatt ccaagctgac agtggataag | 1260 |
| agccggtggc agcagggcaa cgtgttctcc tgttctgtga tgcacgaggc actgcacaat | 1320 |
| cattacaccc agaaatccct gtcactgagc cccggcaag | 1359 |

<210> SEQ ID NO 38
<211> LENGTH: 1350
<212> TYPE: DNA
<213> ORGANISM: Artificial Sequence
<220> FEATURE:
<223> OTHER INFORMATION: Synthetic construct

<400> SEQUENCE: 38

| | |
|---|---|
| caggtccagc tggtgcagag cggggcagag gtcaagaaac ccggtagctc cgtgaaggtc | 60 |
| agctgcaagg cttccggcgg aaccttctct agttacgcca tcagctgggt gagacaggct | 120 |
| cctggccagg gactggaatg gatgggcctg atcattccat cttttgatac cgctggctac | 180 |
| gcacagaagt tcagggacg ggtggcaatt acagtcgatg agtcaaccag cacagcctat | 240 |
| atggagctgt caagcctgcg gtccgaagac actgccgtgt actattgcgc aagggccgaa | 300 |
| cactcctcta ctggaaccctt cgattactgg gggcagggta ccctggtgac agtcagttca | 360 |
| gccagcacta agggacccag cgtgtttcca gaggccccct ctagtaaatc cacttctgga | 420 |
| ggcaccgctg cactgggctg tctggtgacc gattacttcc cagagccgt cacagtgagc | 480 |
| tggaactccg ggccctgac agcggagtc catacatttc ctgctgtgct ggagtcaagc | 540 |
| gggctgtact ccctgtcctc tgtggtcacc gtgccaagtt caagcctggg aactcagacc | 600 |
| tatatctgca acgtgaatca caagccttca aatacaaaag ttgacaaacg tgtggaaccc | 660 |
| aagagttgtg ataaaaccca tacatgcccc ccttgtccgg cgccagaggc tgcaggagga | 720 |
| ccaagcgtgt tcctgtttcc acccaagcct aaagacacac tgatgatttc ccgaaccccc | 780 |
| gaagtcacat gcgtggtcgt gtctgtgagt cacgaggacc ctgaagtcaa gttcaactgg | 840 |
| tacgtggatg gcgtcgaggt gcataatgcc aagactaaac ctagggagga acagtacaac | 900 |
| tcaacctatc gcgtcgtgag cgtcctgaca gtgctgcacc aggattggct gaacggcaaa | 960 |
| gaatataagt gcaaagtgag caataaggcc ctgcccgctc ctatcgagaa accatttcc | 1020 |
| aaggctaaag gcagcctcg cgaaccacag gtctacgtgc tgcctccatc ccgggacgag | 1080 |
| ctgacaaaga accaggtctc tctgctgtgc ctggtgaaag gcttctatcc atcagatatt | 1140 |
| gctgtggagt gggaaagcaa tgggcagccc gagaacaatt acctgacttg gccccctgtg | 1200 |
| ctggactctg atgggagttt cttctctgtat tctaagctga ccgtggataa agtaggtgg | 1260 |
| cagcagggaa atgtctttag ttgttcagtg atgcatgaag ccctgcataa ccactacacc | 1320 |
| cagaaaagcc tgtccctgtc ccccggaaaa | 1350 |

<210> SEQ ID NO 39
<211> LENGTH: 1350

<212> TYPE: DNA
<213> ORGANISM: Artificial Sequence
<220> FEATURE:
<223> OTHER INFORMATION: Synthetic construct

<400> SEQUENCE: 39

```
caggtccagc tggtgcagag cggggcagag gtcaagaaac ccggtagctc cgtgaaggtc    60
agctgcaagg cttccggcgg aaccttctct agttacgcca tcagctgggt gagacaggct   120
cctggccagg gactggaatg gatgggcctg atcattccaa tgttcgacac cgctggctac   180
gcacagaagt ttcagggacg ggtggcaatt acagtcgatg agtcaaccag cacagcctat   240
atggagctgt caagcctgcg gtccgaagac actgccgtgt actattgcgc aagggccgaa   300
cactcctcta ctggaacctt cgattactgg gggcaggta cctggtgac agtcagttca    360
gccagcacta agggacccag cgtgtttcca gaggcccct ctagtaaatc cacttctgga    420
ggcaccgctg cactgggctg tctggtgacc gattacttcc cagagcccgt cacagtgagc   480
tggaactccg ggccctgac cagcggagtc catacatttc ctgctgtgct ggagtcaagc   540
gggctgtact ccctgtcctc tgtggtcacc gtgccaagtt caagcctggg aactcagacc   600
tatatctgca acgtgaatca caagccttca atacaaaag ttgacaaacg tgtggaaccc    660
aagagttgtg ataaaaccca tacatgcccc ccttgtccgg cgccagaggc tgcaggagga   720
ccaagcgtgt tcctgtttcc acccaagcct aaagacacac tgatgatttc cgaaccccc    780
gaagtcacat gcgtggtcgt gtctgtgagt cacgaggacc ctgaagtcaa gttcaactgg   840
tacgtggatg gcgtcgaggt gcataatgcc aagactaaac ctagggagga acagtacaac   900
tcaacctatc gcgtcgtgag cgtcctgaca gtgctgcacc aggattggct gaacggcaaa   960
gaatataagt gcaaagtgag caataaggcc ctgcccgctc ctatcgagaa aaccatttcc  1020
aaggctaaag ggcagcctcg cgaaccacag gtctacgtgt atcctccaag ccgggacgag  1080
ctgacaaaga accaggtctc cctgacttgt ctggtgaaag ggttttaccc tagtgatatc  1140
gctgtggagt gggaatcaaa tggacagcca gagaacaatt ataagactac ccccctgtg   1200
ctggacagtg atgggtcatt cgcactggtc tccaagctga cagtggacaa atctcggtgg  1260
cagcagggaa atgtcttttc atgtagcgtg atgcatgaag cactgcacaa ccattacacc  1320
cagaagtcac tgtcactgtc accaggaaaa                                   1350
```

<210> SEQ ID NO 40
<211> LENGTH: 330
<212> TYPE: PRT
<213> ORGANISM: Homo sapiens

<400> SEQUENCE: 40

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95
```

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 41
<211> LENGTH: 280
<212> TYPE: PRT
<213> ORGANISM: Artificial Sequence
<220> FEATURE:
<223> OTHER INFORMATION: Synthetic construct

<400> SEQUENCE: 41

His Thr Phe Pro Ala Val Leu Gln Ser Ser Gly Leu Tyr Ser Leu Lys
1               5                   10                  15

Ser Val Val Thr Val Pro Ser Ser Leu Gly Thr Gln Thr Tyr Ile
            20                  25                  30

Cys Asn Val Asn His Lys Pro Ser Asn Thr Lys Val Asp Lys Arg Val
            35                  40                  45

Glu Pro Lys Ser Cys Asp Lys Thr His Thr Cys Pro Pro Cys Pro Ala
50                  55                  60

Pro Glu Ala Ala Gly Gly Pro Ser Val Phe Leu Phe Pro Pro Lys Pro
65                  70                  75                  80

Lys Asp Thr Leu Met Ile Ser Arg Thr Pro Glu Val Thr Cys Val Val
                85                  90                  95

Val Ser Val Ser His Glu Asp Pro Glu Val Lys Phe Asn Trp Tyr Val
            100                 105                 110

Asp Gly Val Glu Val His Asn Ala Lys Thr Lys Pro Arg Glu Glu Gln
            115                 120                 125

Tyr Asn Ser Thr Tyr Arg Val Val Ser Val Leu Thr Val Leu His Gln
            130                 135                 140

Asp Trp Leu Asn Gly Lys Glu Tyr Lys Cys Lys Val Ser Asn Lys Ala
145                 150                 155                 160

Leu Pro Ala Pro Ile Glu Lys Thr Ile Ser Lys Ala Lys Gly Gln Pro
                165                 170                 175

Arg Glu Pro Gln Val Tyr Val Tyr Pro Ser Arg Asp Glu Leu Thr
                180                 185                 190

Lys Asn Gln Val Ser Leu Thr Cys Leu Val Lys Gly Phe Tyr Pro Ser
            195                 200                 205

Asp Ile Ala Val Glu Trp Glu Ser Asn Gly Gln Pro Glu Asn Asn Tyr
210                 215                 220

Lys Thr Thr Pro Pro Val Leu Asp Ser Asp Gly Ser Phe Ala Leu Val
225                 230                 235                 240

Ser Lys Leu Thr Val Asp Lys Ser Arg Trp Gln Gln Gly Asn Val Phe
                245                 250                 255

Ser Cys Ser Val Met His Glu Ala Leu His Asn His Tyr Thr Gln Lys
            260                 265                 270

Ser Leu Ser Leu Ser Pro Gly Lys
            275                 280

<210> SEQ ID NO 42
<211> LENGTH: 330
<212> TYPE: PRT
<213> ORGANISM: Artificial Sequence
<220> FEATURE:
<223> OTHER INFORMATION: Synthetic construct

<400> SEQUENCE: 42

Ala Ser Thr Lys Gly Pro Ser Val Phe Pro Glu Ala Pro Ser Ser Lys
1               5                   10                  15

Ser Thr Ser Gly Gly Thr Ala Ala Leu Gly Cys Leu Val Thr Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Glu Ser Ser Gly Leu Tyr Ser
50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
                100                 105                 110

Pro Ala Pro Glu Ala Ala Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Ser Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

```
Lys Ala Leu Pro Ala Pro Ile Glu Lys Thr Ile Ser Lys Ala Lys Gly
    210                 215                 220

Gln Pro Arg Glu Pro Gln Val Tyr Val Tyr Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Ala
        275                 280                 285

Leu Val Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 43
<211> LENGTH: 330
<212> TYPE: PRT
<213> ORGANISM: Artificial Sequence
<220> FEATURE:
<223> OTHER INFORMATION: Synthetic construct

<400> SEQUENCE: 43

Ala Ser Thr Lys Gly Pro Ser Val Phe Pro Glu Ala Pro Ser Ser Lys
1               5                   10                  15

Ser Thr Ser Gly Gly Thr Ala Ala Leu Gly Cys Leu Val Thr Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Glu Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
    115                 120                 125

Lys Pro Lys Asp Thr Leu Met Ile Ser Arg Thr Pro Glu Val Thr Cys
130                 135                 140

Val Val Val Ser Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
    195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Val Leu Pro Pro Ser Arg Asp Glu
225                 230                 235                 240
```

```
Leu Thr Lys Asn Gln Val Ser Leu Leu Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Leu Thr Trp Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 44
<211> LENGTH: 330
<212> TYPE: PRT
<213> ORGANISM: Artificial Sequence
<220> FEATURE:
<223> OTHER INFORMATION: Synthetic construct

<400> SEQUENCE: 44

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Lys Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Ser Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Val Leu Pro Pro Ser Arg Asp Glu
225                 230                 235                 240

Leu Thr Lys Asn Gln Val Ser Leu Leu Cys Leu Val Lys Gly Phe Tyr
                245                 250                 255

Pro Ser Asp Ile Ala Val Glu Trp Glu Ser Asn Gly Gln Pro Glu Asn
            260                 265                 270
```

```
Asn Tyr Leu Thr Trp Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 45
<211> LENGTH: 105
<212> TYPE: PRT
<213> ORGANISM: Homo sapiens

<400> SEQUENCE: 45

Gln Pro Lys Ala Asn Pro Thr Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Gly Ser Pro Val
        35                  40                  45

Lys Ala Gly Val Glu Thr Thr Lys Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 46
<211> LENGTH: 105
<212> TYPE: PRT
<213> ORGANISM: Artificial Sequence
<220> FEATURE:
<223> OTHER INFORMATION: Synthetic construct

<400> SEQUENCE: 46

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Glu Ser Glu Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Ala Glu Cys Ser
            100                 105

<210> SEQ ID NO 47
<211> LENGTH: 107
<212> TYPE: PRT
<213> ORGANISM: Homo sapiens

<400> SEQUENCE: 47
```

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65              70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 48
<211> LENGTH: 107
<212> TYPE: PRT
<213> ORGANISM: Artificial Sequence
<220> FEATURE:
<223> OTHER INFORMATION: Synthetic construct

<400> SEQUENCE: 48

Arg Thr Val Ala Ala Pro Ser Val Phe Ile Phe Pro Pro Ser Asp Glu
1               5                   10                  15

Gln Leu Lys Ser Gly Thr Ala Arg Val Gly Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Arg Ser Thr Leu Thr Leu Ser Lys Ala Asp Tyr Glu
65              70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 49
<211> LENGTH: 453
<212> TYPE: PRT
<213> ORGANISM: Artificial Sequence
<220> FEATURE:
<223> OTHER INFORMATION: Synthetic construct

<400> SEQUENCE: 49

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65              70                  75                  80

Met Glu Leu Ser Ser Leu Arg Ser Glu Asp Thr Ala Val Tyr Tyr Cys 85            90                95

Ala Arg Ser Pro Asp Tyr Ser Pro Tyr Tyr Tyr Gly Met Asp Val
            100                 105             110

Trp Gly Gln Gly Thr Thr Val Thr Val Ser Ser Ala Ser Thr Lys Gly
            115                 120             125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Lys Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Arg Val Glu Pro Lys
            210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Ser Val
                260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
            290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Val Tyr Pro Pro Ser Arg Asp Glu Leu Thr Lys Asn Gln
            355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Ala Leu Val Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys
    450

<210> SEQ ID NO 50
<211> LENGTH: 648
<212> TYPE: DNA
<213> ORGANISM: Artificial Sequence
<220> FEATURE:
<223> OTHER INFORMATION: Synthetic construct

<400> SEQUENCE: 50

```
cagtctgtgc tgactcagcc accttccgcc tctggaaccc caggacagag ggtcacaatc    60
agttgctcag ggagctcctc taacattgga agcaacactg tgaattggta ccagcagctg   120
cctgggaccg ctccaaagct gctgatctat ggcaactcca atcgaccatc tggagtgcct   180
gaccggttca gcggctccaa atctggcacc agtgcttcac tggcaattag tggcctgcag   240
tccgaggacg aagccgatta ctattgccag agctacgata gttcactgag cggctccgtg   300
ttcggcgggg gaatcaagct gacagtcctg ggacagccaa agcggcgcc cagcgtgact    360
ctgtttccac ccagctccga ggaactgcag gccaataagg ctaccctggt ctgtctgatt   420
tccgacttct accccggggc tgtgacagtc gcatggaagg ccgattctag tcctgtgaaa   480
gcaggagtcg agaccacaac tccatcaaag cagagcaaca caagtacgc agccgagagc    540
gagctgtctc tgacacctga acagtggaaa agccaccggt cttatagttg tcaggtgact   600
cacgagggct caacagtgga aaagacagtc gcacccgcag aatgctca               648
```

<210> SEQ ID NO 51
<211> LENGTH: 1359
<212> TYPE: DNA
<213> ORGANISM: Artificial Sequence
<220> FEATURE:
<223> OTHER INFORMATION: Synthetic construct

<400> SEQUENCE: 51

```
caggtccagc tggtgcagag cggagccgaa gtgaagaaac caggcagctc cgtcaaggtg    60
tcatgcaaag ccagcggcgg gactttctct agttacgcta tctcctgggt gagacaggca   120
ccaggacagg gactggagtg gatgggagga atcattccta tcttcgggac agctaactac   180
gcacagaagt ttcagggaag ggtgactatt accgccgaca atctacaag tactgcttat    240
atggagctgt caagcctgag gagcgaagat accgcagtgt actattgcgc ccgctccccc   300
gactactctc cttactatta ctatggcatg gacgtgtggg ggcagggaac cacagtcaca   360
gtgtcctctg ccagcactaa ggggccttca gtgtttccac tggcacccag ttcaaaatca   420
acaagcggag gaactgccgc tctgggatgt ctggtgaagg actatttccc agagccagtc   480
accgtgagct ggaactccgg cgcactgact tccggagtcc acacctttcc agccgtgctg   540
cagagctccg gactgtactc tctgaagagt gtggtcacag tgccttcaag ctccctgggc   600
acccagacat atatctgcaa cgtgaatcac aagcctagta atactaaggt tgacaaacgt   660
gtggaaccaa agagctgtga taaaactcat acctgccccc cttgtccggc gccagaggca   720
gcaggaggac aagcgtgtt cctgtttcca cccaagccca agacaccct gatgattagc     780
cgaacccctg aagtcacatg cgtggtcgtg tccgtgtctc acgaggaccc agaagtcaag   840
ttcaactggt acgtggatgg cgtcgaggtg cataatgcca agacaaaacc ccgggaggaa   900
cagtacaaca gcacctatag agtcgtgtcc gtcctgacag tgctgcacca ggattggctg   960
aacggcaagg aatataagtg caaagtgtcc aataaggccc tgcccgctcc tatcgagaaa  1020
accatttcta aggcaaaagg ccagcctcgc gaaccacagg tctacgtgta tcctccaagc  1080
cgggacgagc tgacaaagaa ccaggtctcc ctgacttgtc tggtgaaagg gttttaccct  1140
agtgatatcg ctgtggagtg ggaatcaaat ggacagccag agaacaatta taagactacc  1200
```

```
ccccctgtgc tggacagtga tgggtcattc gcactggtct ccaagctgac agtggacaaa    1260
tctcggtggc agcagggaaa tgtcttttca tgtagcgtga tgcatgaagc actgcacaac    1320 cattcaccc agaagtcact gtcactgtca ccaggaaaa                            1359
```

CHECKPOINT INHIBITOR BISPECIFIC ANTIBODIES

The present invention relates to the field of medicine. More particularly, the present invention relates to bispecific antibodies that bind human programmed cell death 1 (PD-1) and human PD-1 ligand 1 (PD-L1), and may be useful for treating solid and hematological tumors alone and in combination with chemotherapy and other cancer therapeutics.

Immune checkpoint pathways are used in maintenance of self-tolerance and control of T cell activation, but cancer cells can use the pathways to suppress the anti-tumor response and prevent their destruction. The PD-1/PD-L1 pathway is one such immune checkpoint. Human PD-1 is found on T cells and human PD-L1 is aberrantly expressed by a variety of tumor types; binding of PD-L1 to PD-1 inhibits T cell proliferation and cytokine production. The PD-1/PD-L1 inhibitory axis has been subjugated by tumors as part of the natural selective process that shapes tumor evolution in the context of an anti-tumor immune response.

While therapeutics targeting the PD-1/PD-L1 pathway are clinically validated and have led to significant clinical advances for treatment of cancer, only a fraction of patients have benefited from such a treatment (see, for example, Sharma, P. and Allison, J. P., Immune checkpoint targeting in cancer therapy: toward combination strategies with curative potential. Cell. 2015; 161:2015-14). For example, only ~20% of the patients with non-small cell lung cancer (NSCLC) responded to PD-1 antibody treatment.

Although clinical trials involving co-administration of a PD-L1 antibody and a PD-1 antibody are currently underway (see, for example, EUROPEAN SOCIETY FOR MEDICAL ONCOLOGY (ESMO) Abstract #2130; October 2016), these treatment regimens involve infusions of two separate antibody products at relatively high dosages for each antibody. Furthermore, it is not known yet if such combination therapies will provide improvements in efficacy without exacerbating the adverse event profile as compared to monotherapy.

WO2017/087547 specifically discloses anti-PD-L1 antibodies and generally discloses heterodimeric molecules (e.g., a bispecific agent) comprising a PD-L1-binding agent described therein and "a second immunotherapeutic agent". In some embodiments the second immunotherapeutic agent may include "an antibody that blocks immunosuppressive functions" such as an "anti-PD-antibody". However, no specific PD-L1/PD-1 bispecific agents were disclosed in this publication. Thus, a bispecific antibody that binds PD-L1 and PD-1 with high affinity, effectively neutralizes PD-L1 and PD-1 activation by all PDx family ligands, and/or provides superior activity relative to known therapeutics targeting the PD-1/PD-L1 pathway, or even combinations thereof, is needed as a more effective pharmacological intervention for certain cancers. Particularly, desirable are such anti-PD-L1/PD-1 bispecific antibodies that i) may more effectively treat cancers characterized as having moderate or high PD-L1 or PD-1 expression levels and ii) demonstrate in vivo stability, physical and chemical stability including, but not limited to, thermal stability, solubility, low self-association, and pharmacokinetic characteristics which are acceptable for development and/or use in the treatment of cancer.

Accordingly, the present invention provides novel heterodimeric bispecific antibodies that can target PD-L1 and PD-1 simultaneously, via the pairing of two different heavy chains and two different light chains into a single IgG-like antibody. Furthermore, the present invention provides anti-human PD-L1 and anti-human PD-1 heterodimeric bispecific antibodies that possess one or more of the following features: block all three interactions of the PD axis (PD-L1 binding to PD-1, PD-L2 binding to PD-1 and PD-L1 binding to CD80), bridge PD-L1 and PD-1 over-expressing cells, increase T cell activation and tumor cell killing due to proximity of bound T cell and tumor cell, demonstrate significant antitumor activity at surprisingly low dosages in tumor cells with moderate to high PD ligand expression levels, and demonstrate unexpected physical and chemical stability including, but not limited to, in vivo stability, thermal stability, solubility, low self-association, and pharmacokinetic characteristics.

Accordingly, the present invention provides an antibody that binds human PD-L1 (SEQ ID NO: 1) and human PD-1 (SEQ ID NO: 2) comprising:
a) a first heavy chain (HC1) comprising a heavy chain variable region (HCVR) comprising the amino acid sequence of SEQ ID NO: 3;
b) a first light chain (LC1) comprising a light chain variable region (LCVR) comprising the amino acid sequence of SEQ ID NO: 4;
c) a second heavy chain (HC2) comprising a heavy chain variable region comprising the amino acid sequence of SEQ ID NO: 5; and
d) a second light chain (LC2) comprising a light chain variable region comprising the amino acid sequence of SEQ ID NO: 8.

The present invention provides an antibody that binds human PD-L1 (SEQ ID NO: 1) and human PD-1 (SEQ ID NO: 2), comprising a HC1, a LC1, a HC2, and a LC2, wherein:
a) said HC1 comprises a CDR1 having the amino acid sequence of SEQ ID NO: 16, a CDR2 having the amino acid sequence of SEQ ID NO: 17, and a CDR3 having the amino acid sequence of SEQ ID NO: 18 in the HCVR;
b) said LC1 comprises a CDR1 having the amino acid sequence of SEQ ID NO: 19, a CDR2 having the amino acid sequence of SEQ ID NO: 20, and a CDR3 having the amino acid sequence of SEQ ID NO: 21 in the LCVR;
c) said HC2 comprises a CDR1 having the amino acid sequence of SEQ ID NO: 22, a CDR2 having the amino acid sequence of SEQ ID NO: 23 or SEQ ID NO: 24, and a CDR3 having the amino acid sequence of SEQ ID NO: 25 in the HCVR;
d) said LC2 comprises a CDR1 having the amino acid sequence of SEQ ID NO: 26, a CDR2 having the amino acid sequence of SEQ ID NO: 27, and a CDR3 having the amino acid sequence of SEQ ID NO: 28 in the LCVR;
e) the CH1 domain of the HC1 comprises an amino acid substitution of S183K;
f) the constant region of the LC1 is a human lambda variant comprising amino acid substitutions of S176E and Y178E;
g) the CH1 domain of the HC2 comprises amino acid substitutions of L128E, K147T, and Q175E;
h) the constant region of the LC2 is a human kappa variant comprising amino acid substitutions of S131R, V133G, and S176R; and
i) the CH3 domain of the HC1 comprises amino acid substitutions of T350V, L351Y, F405A, and Y407V and the CH3 domain of the HC2 comprises amino acid substitutions of T350V, T366L, K392L, and T394W; or the CH3 domain of the HC1 comprises amino acid substitutions of T350V, T366L, K392L, and T394W and the CH3 domain of the HC2 comprises amino acid substitutions of T350V, L351Y, F405A, and Y407V; and, j) wherein the HC1 and HC2 are immune effector function null human IgG1 Fc variants, wherein the numbering is according to the EU index. Preferably, the HC1 and HC2 comprise amino acid substitutions of L234A, L235A, and D265S.

The present invention provides an antibody that binds human PD-L1 (SEQ ID NO: 1) and human PD-1 (SEQ ID NO: 2) comprising:
a) a HC1 comprising, in order from the N-terminus to the C-terminus, the HCVR comprising the amino acid sequence of SEQ ID NO: 3, the amino acid sequence of SEQ ID NO: 9 in the CH1 domain, the amino acid sequence of SEQ ID NO: 10 in the CH2 domain, and the amino acid sequence of SEQ ID NO: 11 or SEQ ID NO: 12 in the CH3 domain;
b) a LC1 comprising, in order from the N-terminus to the C-terminus, the LCVR comprising the amino acid sequence of SEQ ID NO: 4 and the amino acid sequence of SEQ ID NO: 14 in the constant region;
c) a HC2 comprising, in order from the N-terminus to the C-terminus, the HCVR comprising the amino acid sequence of SEQ ID NO: 5, the amino acid sequence of SEQ ID NO: 13 in the CH1 domain, the amino acid sequence of SEQ ID NO: 10 in the CH2 domain, and the amino acid sequence of SEQ ID NO: 12 or the amino acid sequence of SEQ ID NO: 11 in the CH3 domain; and
d) the LC2 comprising, in order from N-terminus, the LCVR comprising the amino acid sequence of SEQ ID NO: 8 and the amino acid sequence of SEQ ID NO: 15 in the constant region, provided that when the amino acid sequence of SEQ ID NO: 11 is present in the CH3 domain of said HC1, the amino acid sequence of SEQ ID NO: 12 is present in the CH3 domain of said HC2; or when the amino acid sequence of SEQ ID NO: 12 is present in the CH3 domain of said HC1, the amino acid sequence of SEQ ID NO: 11 is present in the CH3 domain of said HC2.

The present invention further provides an antibody comprising a HC1, LC1, HC2, and LC2 wherein:
a) said HC1 comprises, in order from the N-terminus to the C-terminus, a HCVR comprising the amino acid sequence of SEQ ID NO: 3, the amino acid sequence of SEQ ID NO: 9 in the CH1 domain, the amino acid sequence of SEQ ID NO: 10 in the CH2 domain, and the amino acid sequence of SEQ ID NO: 11 in the CH3 domain;
b) said LC1 comprising, in order from the N-terminus to the C-terminus, a LCVR comprising the amino acid sequence of SEQ ID NO: 4, and the amino acid sequence of SEQ ID NO: 14 in the constant region; and
c) said HC2 comprising, in order from the N-terminus to the C-terminus, a HCVR comprising the amino acid sequence of SEQ ID NO: 6 the amino acid sequence of SEQ ID NO: 13 in the CH1 domain, the amino acid sequence of SEQ ID NO: 10 in the region of the CH2 domain, and the amino acid sequence of SEQ ID NO: 12 in the CH3 domain; and
d) said LC2 comprising, in order from N-terminus, a LCVR comprising the amino acid sequence of SEQ ID NO: 8, and the amino acid sequence of SEQ ID NO: 15 in the constant region.

The present invention provides an antibody that binds human PD-L1 (SEQ ID NO: 1) and human PD-1 (SEQ ID NO: 2) comprising:
a) a HC1 comprising the amino acid sequence of SEQ ID NO: 49;
b) a LC1 comprising the amino acid sequence of SEQ ID NO: 30;
c) a HC2 comprising the amino acid sequence of SEQ ID NO 31; and
d) a LC2 comprising the amino acid sequence of SEQ ID NO: 34.

The present invention provides an antibody that binds human PD-L1 (SEQ ID NO: 1) and human PD-1 (SEQ ID NO: 2) comprising:
a) a HC1 comprising the amino acid sequence of SEQ ID NO: 49;
b) a LC1 comprising the amino acid sequence of SEQ ID NO: 30;
c) a HC2 comprising the amino acid sequence of SEQ ID NO 33: and
d) a LC2 comprising the amino acid sequence of SEQ ID NO: 34.

The present invention provides an antibody that binds human PD-L1 (SEQ ID NO: 1) and human PD-1 (SEQ ID NO: 2) comprising:
a) a HC1 comprising the amino acid sequence of SEQ ID NO: 29;
b) a LC1 comprising the amino acid sequence of SEQ ID NO: 30;
c) a HC2 comprising the amino acid sequence of SEQ ID NO: 33: and
d) a LC2 comprising the amino acid sequence of SEQ ID NO: 34.

The present invention provides a mammalian cell comprising a DNA molecule comprising a polynucleotide sequence encoding polypeptides having the amino acid sequences of SEQ ID NO: 49, SEQ ID NO: 30, SEQ ID NO: 31, and SEQ ID NO: 34, wherein the cell is capable of expressing an antibody of the present invention.

The present invention provides a mammalian cell comprising a DNA molecule comprising a polynucleotide sequence encoding polypeptides having the amino acid sequences of SEQ ID NO: 49, SEQ ID NO: 30, SEQ ID NO: 33, and SEQ ID NO: 34, wherein the cell is capable of expressing an antibody of the present invention.

The present invention provides a mammalian cell comprising a DNA molecule comprising a polynucleotide sequence encoding polypeptides having the amino acid sequences of SEQ ID NO: 29, SEQ ID NO: 30, SEQ ID NO: 33, and SEQ ID NO: 34, wherein the cell is capable of expressing an antibody of the present invention.

The present invention provides a process for producing an antibody of the present invention comprising cultivating a mammalian cell of the present invention under conditions such that the antibody is expressed, and recovering the expressed antibody.

The present invention provides an antibody produced by a process of the present invention.

The present invention provides a pharmaceutical composition, comprising an antibody of the present invention and an acceptable carrier, diluent, or excipient.

The present invention provides a method of treating cancer, comprising administering to a patient in need thereof, an effective amount of an antibody of the present invention. The present invention further provides a method of treating cancer wherein said method comprises administering to a patient in need thereof, an effective amount of an antibody of the present invention, wherein the cancer is Hodgkin's or non-Hodgkin's lymphomas, melanoma, renal cell cancer, kidney cancer, lung cancer, bladder cancer, gastric and esophageal cancer, colorectal cancer, liver cancer, hepatocellular cancer, cholangiocarcinoma, pancreatic cancer, breast cancer, triple-negative breast cancer, ovarian cancer, endometrial cancer, prostate cancer, small cell lung cancer (SCLC), non-small cell lung cancer (NSCLC), mesothelioma, squamous cancer of head neck cancer (SCCHN), soft tissue sarcoma, or glioblastoma multiforme.

The present invention provides a method of treating cancer, wherein the cancer is melanoma. The present invention further provides a method of treating cancer, wherein the cancer is lung cancer. The present invention further provides a method of treating cancer, wherein the lung cancer is NSCLC (squamous and non-squamous), small cell lung cancer, or mesothelioma. The present invention further provides a method of treating cancer, wherein the cancer is head and neck cancer. The present invention further provides a method of treating cancer, wherein the cancer is liver cancer. The present invention further provides a method of treating cancer, wherein the cancer is colorectal cancer. The present invention further provides a method of treating cancer, wherein the cancer is pancreatic cancer. The present invention further provides a method of treating cancer, wherein the cancer is gastric cancer. The present invention further provides a method of treating cancer, wherein the cancer is kidney cancer. The present invention further provides a method of treating cancer, wherein the cancer is bladder cancer. The present invention further provides a method of treating cancer, wherein the cancer is prostate cancer. The present invention further provides a method of treating cancer, wherein the cancer is breast cancer. The present invention further provides a method of treating cancer, wherein the cancer is ovarian cancer. The present invention further provides a method of treating cancer, wherein the cancer is endometrial cancer. The present invention further provides a method of treating cancer, wherein the cancer is esophageal cancer. The present invention further provides a method of treating cancer, wherein the cancer is soft tissue sarcoma. The present invention further provides a method of treating cancer, wherein the cancer is cholangiocarcinoma. The present invention further provides a method of treating cancer, wherein the cancer is hepatocellular carcinoma.

The present invention further provides methods comprising the administration of an effective amount of the antibody of the present invention in simultaneous, separate, or sequential combination with one or more anti-tumor agents selected from the group consisting of cisplatin, carboplatin, dacarbazine, liposomal doxorubicin, docetaxel, cyclophosphamide and doxorubicin, navelbine, eribulin, paclitaxel, paclitaxel protein-bound particles for injectable suspension, ixabepilone, capecitabine, FOLFOX (leucovorin, fluorouracil, and oxaliplatin), FOLFIRI (leucovorin, fluorouracil, and irinotecan), gemcitabine, topotecan, liposomal irinotecan, pemetrexed, cetuximab, nivolumab, ipilimumab, pidilizumab, pembrolizumab, tremelimumab, urelumab, lirilumab, atezolizumab, epacadostat, and durvalumab.

The present invention further provides methods comprising the administration of an effective amount of the antibody of the present invention comprising simultaneous, separate, or sequential combination with ionizing radiation.

The present invention provides an antibody of the present invention, for use in therapy. The present invention provides an antibody of the present invention, for use in the treatment of cancer. The present invention provides an antibody of the present invention, for use in the treatment of cancer, wherein the cancer is Hodgkin's or non-Hodgkin's lymphomas, melanoma, renal cell cancer, kidney cancer, lung cancer, bladder cancer, gastric and esophageal cancer, colorectal cancer, liver cancer, hepatocellular cancer, cholangiocarcinoma, pancreatic cancer, breast cancer, triple-negative breast cancer, ovarian cancer, endometrial cancer, prostate cancer, small cell lung cancer (SCLC), non-small cell lung cancer (NSCLC), mesothelioma, squamous cancer of head neck cancer (SCCHN), soft tissue sarcoma, or glioblastoma multiforme.

The present invention provides an antibody of the present invention, for use in the treatment of melanoma. The present invention provides an antibody of the present invention, for use in the treatment of lung cancer. The present invention further provides an antibody of the present invention, wherein the lung cancer is NSCLC (squamous and non-squamous), small cell lung cancer, or mesothelioma. The present invention provides an antibody of the present invention, for use in the treatment of head and neck cancer. The present invention provides an antibody of the present invention, for use in the treatment of liver cancer. The present invention provides an antibody of the present invention, for use in the treatment of colorectal cancer. The present invention provides an antibody of the present invention, for use in the treatment of pancreatic cancer. The present invention provides an antibody of the present invention, for use in the treatment of gastric cancer. The present invention provides an antibody of the present invention, for use in the treatment of kidney cancer. The present invention provides an antibody of the present invention, for use in the treatment of bladder cancer. The present invention provides an antibody of the present invention, for use in the treatment of prostate cancer. The present invention provides an antibody of the present invention, for use in the treatment of breast cancer. The present invention provides an antibody of the present invention, for use in the treatment of ovarian cancer. The present invention provides an antibody of the present invention, for use in the treatment of endometrial cancer. The present invention provides an antibody of the present invention, for use in the treatment of esophageal cancer. The present invention provides an antibody of the present invention, for use in the treatment of soft tissue sarcoma. The present invention provides an antibody of the present invention, for use in the treatment of cholangiocarcinoma. The present invention provides an antibody of the present invention, for use in the treatment of hepatocellular carcinoma.

The present invention provides the antibody of the present invention for use in simultaneous, separate, or sequential combination with one or more anti-tumor agents selected from the group consisting of cisplatin, carboplatin, dacarbazine, liposomal doxorubicin, docetaxel, cyclophosphamide and doxorubicin, navelbine, eribulin, paclitaxel, paclitaxel protein-bound particles for injectable suspension, ixabepilone, capecitabine, FOLFOX (leucovorin, fluorouracil, and oxaliplatin), FOLFIRI (leucovorin, fluorouracil, and irinotecan), gemcitabine, topotecan, liposomal irinotecan, pemetrexed, cetuximab, nivolumab, ipilimumab, pidilizumab, pembrolizumab, tremelimumab, urelumab, lirilumab, atezolizumab, epacadostat, and durvalumab, in the treatment of cancer.

The present invention provides the antibody of the present invention for use in simultaneous, separate, or sequential combination with ionizing radiation, in the treatment of cancer.

The present invention provides a pharmaceutical composition for use in treating cancer, comprising an effective amount of an antibody of the present invention. The present invention further provides a pharmaceutical composition for use in treating cancer, comprising an effective amount of an antibody of the present invention, wherein the cancer is Hodgkin's or non-Hodgkin's lymphomas, melanoma, renal cell cancer, kidney cancer, lung cancer, bladder cancer, gastric and esophageal cancer, colorectal cancer, liver cancer, hepatocellular cancer, cholangiocarcinoma, pancreatic cancer, breast cancer, triple-negative breast cancer, ovarian cancer, endometrial cancer, prostate cancer, small cell lung cancer (SCLC), non-small cell lung cancer (NSCLC), mesothelioma, squamous cancer of head neck cancer (SCCHN), soft tissue sarcoma, or glioblastoma multiforme. The present invention further provides a pharmaceutical composition for use in treating cancer, comprising an effective amount of an antibody of the present invention, wherein the lung cancer is NSCLC (squamous and non-squamous), small cell lung cancer, or mesothelioma.

The present invention provides a pharmaceutical composition for use in treating melanoma, comprising an effective amount of an antibody of the present invention. The present invention provides a pharmaceutical composition for use in treating lung cancer, including, but not limited to, NSCLC (squamous and non-squamous), small cell lung cancer, or mesothelioma comprising an effective amount of an antibody of the present invention. The present invention provides a pharmaceutical composition for use in treating head and neck cancer, comprising an effective amount of an antibody of the present invention. The present invention provides a pharmaceutical composition for use in treating liver cancer, comprising an effective amount of an antibody of the present invention. The present invention provides a pharmaceutical composition for use in treating colorectal cancer, comprising an effective amount of an antibody of the present invention. The present invention provides a pharmaceutical composition for use in treating pancreatic cancer, comprising an effective amount of an antibody of the present invention. The present invention provides a pharmaceutical composition for use in treating gastric cancer, comprising an effective amount of an antibody of the present invention. The present invention provides a pharmaceutical composition for use in treating kidney cancer, comprising an effective amount of an antibody of the present invention. The present invention provides a pharmaceutical composition for use in treating bladder cancer, comprising an effective amount of an antibody of the present invention. The present invention provides a pharmaceutical composition for use in treating prostate cancer, comprising an effective amount of an antibody of the present invention. The present invention provides a pharmaceutical composition for use in treating breast cancer, comprising an effective amount of an antibody of the present invention. The present invention provides a pharmaceutical composition for use in treating ovarian cancer, comprising an effective amount of an antibody of the present invention. The present invention provides a pharmaceutical composition for use in treating endometrial cancer, comprising an effective amount of an antibody of the present invention. The present invention provides a pharmaceutical composition for use in treating esophageal cancer, comprising an effective amount of an antibody of the present invention. The present invention provides a pharmaceutical composition for use in treating soft tissue sarcoma, comprising an effective amount of an antibody of the present invention. The present invention provides a pharmaceutical composition for use in treating cholangiocarcinoma, comprising an effective amount of an antibody of the present invention. The present invention provides a pharmaceutical composition for use in treating hepatocellular carcinoma, comprising an effective amount of an antibody of the present invention.

The present invention further provides a pharmaceutical composition for use in treating cancer, wherein said pharmaceutical composition is administered in simultaneous, separate, or sequential combination with one or more antitumor agents selected from the group consisting of cisplatin, carboplatin, dacarbazine, liposomal doxorubicin, docetaxel, cyclophosphamide and doxorubicin, navelbine, eribulin, paclitaxel, paclitaxel protein-bound particles for injectable suspension, ixabepilone, capecitabine, FOLFOX (leucovorin, fluorouracil, and oxaliplatin), FOLFIRI (leucovorin, fluorouracil, and irinotecan), gemcitabine, topotecan, liposomal irinotecan, pemetrexed, cetuximab, nivolumab, ipilimumab, pidilizumab, pembrolizumab, tremelimumab, urelumab, lirilumab, atezolizumab, epacadostat, and durvalumab.

The present invention further provides a pharmaceutical composition for use in treating cancer, wherein said pharmaceutical composition is administered in simultaneous, separate, or sequential combination with ionizing radiation.

The present invention provides the use of an antibody of the present invention for the manufacture of a medicament for the treatment of cancer. The present invention further provides the use of an antibody of the present invention for the manufacture of a medicament for the treatment of cancer, wherein the cancer is Hodgkin's or non-Hodgkin's lymphomas, melanoma, renal cell cancer, kidney cancer, lung cancer, bladder cancer, gastric and esophageal cancer, colorectal cancer, liver cancer, hepatocellular cancer, cholangiocarcinoma, pancreatic cancer, breast cancer, triple-negative breast cancer, ovarian cancer, endometrial cancer, prostate cancer, small cell lung cancer (SCLC), non-small cell lung cancer (NSCLC), mesothelioma, squamous cancer of head neck cancer (SCCHN), soft tissue sarcoma, or glioblastoma multiforme. The present invention further provides the use of an antibody of the present invention for the manufacture of a medicament for the treatment of cancer, wherein the lung cancer is NSCLC (squamous and non-squamous), small cell lung cancer, or mesothelioma.

The present invention further provides the use of an antibody of the present invention in the manufacture of a medicament for the treatment of cancer wherein said medicament is to be administered simultaneously, separately, or sequentially with one or more antitumor agents selected from the group consisting of cisplatin, carboplatin, dacarbazine, liposomal doxorubicin, docetaxel, cyclophosphamide and doxorubicin, navelbine, eribulin, paclitaxel, paclitaxel protein-bound particles for injectable suspension, ixabepilone, capecitabine, FOLFOX (leucovorin, fluorouracil, and oxaliplatin), FOLFIRI (leucovorin, fluorouracil, and irinotecan), gemcitabine, topotecan, liposomal irinotecan, pemetrexed, cetuximab, nivolumab, ipilimumab, pidilizumab, pembrolizumab, tremelimumab, urelumab, lirilumab, atezolizumab, epacadostat, and durvalumab.

The present invention provides the use of an antibody of the present invention in the manufacture of a medicament for the treatment of cancer wherein said medicament is to be administered simultaneously, separately, or sequentially with ionizing radiation.

An antibody of the present invention is an engineered, non-naturally occurring polypeptide complex. A DNA molecule of the present invention is a non-naturally occurring DNA molecule that comprises a polynucleotide sequence encoding a polypeptide having the amino acid sequence of one of the polypeptides in an antibody of the present invention.

An antibody of the present invention is an IgG type antibody and has "heavy" chains and "light" chains that are cross-linked via intra- and inter-chain disulfide bonds. Each heavy chain is comprised of an N-terminal HCVR and a heavy chain constant region ("HCCR"). Each light chain is comprised of an N-terminal LCVR and a light chain constant region ("LCCR"). Light chains each form disulfide bonds with a heavy chain, and the two heavy chains form two disulfide bonds between each other.

The constant region of the heavy chains contains CH1, CH2, and CH3 domains. CH1 comes after the HCVR; the CH1 and HCVR form the heavy chain portion of a Fab. CH2 comes after the hinge region and before CH3. CH3 comes after CH2 and is at the carboxy-terminal end of the heavy chain.

The constant region of the light chains contains one domain, CL. CL comes after the LCVR; the CL and LCVR form the light chain portion of a Fab.

Antibodies of the present invention are heterodimeric in that each arm of the antibody exhibits selective monovalent binding to its cognate antigen due to two different heavy chains and two different light chains forming the antibody. In the present invention one arm of the antibody binds human PD-L1 (SEQ ID NO: 1), and the other arm binds human PD-1 (SEQ ID NO: 2). The CH2 and/or CH3 domains of such polypeptide chains need not be identical in sequence, and advantageously are modified to foster complexing between the two polypeptide chains. For example, an amino acid substitution (preferably a substitution with an amino acid comprising a bulky side group forming a "knob", e.g., tryptophan) can be introduced into the CH2 or CH3 domain such that steric interference will prevent interaction with a similarly mutated domain and will obligate the mutated domain to pair with a domain into which a complementary, or accommodating mutation has been engineered, i.e., "the hole" {e.g., a substitution with glycine). Such sets of mutations can be engineered into any pair of polypeptides comprising CH2-CH3 Domains that form an Fc region. Methods of protein engineering to favor heterodimerization over homodimerization are well known in the art, in particular with respect to the engineering of immunoglobulin-like molecules (see e.g., WO 96/27011, WO 98/050431, EP 1870459, WO 2007/110205, WO 2007/147901, WO 2009/089004, WO 2010/129304, WO 2011/90754, WO 2011/143545, WO 2012/058768, WO 2013/157954, WO 2013/096291, EP 1 870 459A1, as well as, Ridgway et al. (1996) "'Knobs-Into-Holes' Engineering Of Antibody CH3 Domains For Heavy Chain Heterodimerization," Protein Engr. 9:617-621, Atwell et al. (1997) "Stable Heterodimers From Remodeling The Domain Interface Of A Homodimer Using A Phage Display Library," J. Mol. Biol. 270: 26-35, and Xie et al. (2005) "A New Format Of Bispecific Antibody: Highly Efficient Heterodimerization, Expression And Tumor Cell Lysis," J. Immunol. Methods 296:95-101). Typically, in the approaches known in the art, the CH3 domain of the first heavy chain and the CH3 domain of the second heavy chain are both engineered in a complementary manner so that the heavy chain comprising one engineered CH3 domain can no longer homodimerize with another heavy chain of the same structure (e.g. a CH3-engineered first heavy chain can no longer homodimerize with another CH3-engineered first heavy chain; and a CH3-engineered second heavy chain can no longer homodimerize with another CH3-engineered second heavy chain). Thereby the heavy chain comprising one engineered CH3 domain is forced to heterodimerize with another heavy chain comprising the CH3 domain, which is engineered in a complementary manner. For this embodiment of the invention, the CH3 domain of the first heavy chain and the CH3 domain of the second heavy chain are engineered in a complementary manner by amino acid substitutions, such that the first heavy chain and the second heavy chain are forced to heterodimerize, whereas the first heavy chain and the second heavy chain can no longer homodimerize (e.g. for steric reasons).

The different approaches for supporting heavy chain heterodimerization known in the art, are contemplated as different alternatives used in a bispecific antibody according to the invention. In some embodiments of the present invention, mutations are incorporated into the sequence of the heavy chains within the CH1 and CH3 region and into the sequence of the light chains within the light chain constant region. The CH1 and LC mutations are made to favor native pairing of the requisite light chain and heavy chain pairs and disfavor light chain mispairing. The CH3 mutations are made to favor heterodimeric pairing of the two distinct heavy chains and disfavor formation of homodimers.

Preferably, when mutations in the CH3 region of the anti-PD-L1 portion of the antibody includes positions 350, 351, 405, and 407 in EU numbering, mutations in the CH3 region of the anti-PD-1 portion of the antibody includes positions 350, 366, 392, and 394 in EU numbering; when mutations in the CH3 region of the anti-PD-L1 portion of the antibody includes positions 350, 366, 392, and 394 in EU numbering, mutations in the CH3 region of the anti-PD-1 portion of the antibody includes positions 350, 351, 356, 405, and 407 in EU numbering (as shown in the sequence alignment shown immediately below).

Alignment of the Amino Acid Sequences of Wild-Type Human IgG1 and the Constant Regions of the Heavy Chain of Antibodies v3.2 and v13884 (Preferred Modifications are Underlined):

```
IgG1-    ASTKGPSVFPLAPSSKSTSGGTAALGCLVKDYFPEPVTVSWNSGA
wt 3.2PD-   ASTKGPSVFPLAPSSKSTSGGTAALGCLVKDYFPEPVTVSWNSGA
L1

844PD-   ASTKGPSVFPEAPSSKSTSGGTAALGCLVTDYFPEPVTVSWNSGA
1

3.2PD-   ASTKGPSVFPEAPSSKSTSGGTAALGCLVTDYFPEPVTVSWNSGA
1

844PD-   ASTKGPSVFPLAPSSKSTSGGTAALGCLVKDYFPEPVTVSWNSGA
L1

IgG1-    LTSGVHTFPAVLQSSGLYSLSSVVTVPSSSLGTQTYICNVNHKP
wt 3.2PD-   LTSGVHTFPAVLQSSGLYSLKSVVTVPSSSLGTQTYICNVNHKP
L1

844PD-   LTSGVHTFPAVLESSGLYSLSSVVTVPSSSLGTQTYICNVNHKP
1

3.2PD-   LTSGVHTFPAVLESSGLYSLSSVVTVPSSSLGTQTYICNVNHKP
1

844PD-   LTSGVHTFPAVLQSSGLYSLKSVVTVPSSSLGTQTYICNVNHKP
L1

IgG1-    SNTKVDKKVEPKSCDKTHTCPPCPAPELLGGPSVFLFPPKPKDTL
wt 3.2PD-   SNTKVDKRVEPKSCDKTHTCPPCPAPEAAGGPSVFLFPPKPKDTL
L1

844PD-   SNTKVDKRVEPKSCDKTHTCPPCPAPEAAGGPSVFLFPPKPKDTL
1

3.2PD-   SNTKVDKRVEPKSCDKTHTCPPCPAPEAAGGPSVFLFPPKPKDTL
1
```

```
844PD-  SNTKVDKRVEPKSCDKTHTCPPCPAPEAAGGPSVFLFPPKPKDTL
L1

IgG1-   MISRTPEVTCVVVDVSHEDPEVKFNWYVDGVEVHNAKTKPREEQY
wt 3.2PD-  MISRTPEVTCVVVSVSHEDPEVKFNWYVDGVEVHNAKTKPREEQY
L1

844PD-  MISRTPEVTCVVVSVSHEDPEVKFNWYVDGVEVHNAKTKPREEQY
1

3.2PD-  MISRTPEVTCVVVSVSHEDPEVKFNWYVDGVEVHNAKTKPREEQY
1

844PD-  MISRTPEVTCVVVSVSHEDPEVKFNWYVDGVEVHNAKTKPREEQY
L1

IgG1-   NSTYRVVSVLTVLHQDWLNGKEYKCKVSNKALPAPIEKTISKAKG
wt 3.2PD-  NSTYRVVSVLTVLHQDWLNGKEYKCKVSNKALPAPIEKTISKAKG
L1

844PD-  NSTYRVVSVLTVLHQDWLNGKEYKCKVSNKALPAPIEKTISKAKG
1

3.2PD-  NSTYRVVSVLTVLHQDWLNGKEYKCKVSNKALPAPIEKTISKAKG
1

844PD-  NSTYRVVSVLTVLHQDWLNGKEYKCKVSNKALPAPIEKTISKAKG
L1

IgG1-   QPREPQVYTLPPSRDELTKNQVSLTCLVKGFYPSDIAVEWESNGQ
wt 3.2PD-  QPREPQVYVYPPSRDELTKNQVSLTCLVKGFYPSDIAVEWESNGQ
L1

844PD-  QPREPQVYVYPPSRDELTKNQVSLTCLVKGFYPSDIAVEWESNGQ
1

3.2PD-  QPREPQVYVLPPSRDELTKNQVSLLCLVKGFYPSDIAVEWESNGQ
1

844PD-  QPREPQVYVLPPSRDELTKNQVSLLCLVKGFYPSDIAVEWESNGQ
L1

IgG1-   PENNYKTTPPVLDSDGSFFLYSKLTVDKSRWQQGNVFSCSVMHEA
wt 3.2PD-  PENNYKTTPPVLDSDGSFALVSKLTVDKSRWQQGNVFSCSVMHEA
L1

844PD-  PENNYKTTPPVLDSDGSFALVSKLTVDKSRWQQGNVFSCSVMHEA
1

3.2PD-  PENNYLTWPPVLDSDGSFFLYSKLTVDKSRWQQGNVFSCSVMHEA
1

844PD-  PENNYLTWPPVLDSDGSFFLYSKLTVDKSRWQQGNVFSCSVMHEA
L1

IgG1-   LHNHYTQKSLSLSPGK              (SEQ ID NO: 40)
wt 3.2PD-  LHNHYTQKSLSLSPGK              (SEQ ID NO: 41)
L1

844PD-  LHNHYTQKSLSLSPGK              (SEQ ID NO: 42)
1

3.2PD-  LHNHYTQKSLSLSPGK              (SEQ ID NO: 43)
1

844PD-  LHNHYTQKSLSLSPGK              (SEQ ID NO: 44)
L1
```

Preferably, as shown underlined in the alignment immediately above, mutations in the CH1 region of the anti-PD-L1 portion of the antibody preferably includes position 183 in EU numbering while mutations in the CH1 region of the anti-PD-1 portion of the antibody preferably includes positions 128, 147, and 175 in EU numbering.

The CL region of the anti-PD-L1 portion of the antibody is preferably a human lambda subtype. More preferably, the CL region of the anti-PD-L1 portion of the antibody is a human lambda variant comprising amino acid substitutions of positions 176 and 178 in EU numbering (see alignment below)

Alignment of the Amino Acid Sequence of Wild-Type Human Lambda with the Constant Region of the PD-L1 Light Chain of the v3.2, v3.0, and v13844 Antibodies or PD-1 (Preferred Modifications are Underlined).

```
Lamb-    QPKANPTVTLFPPSSEELQANKATLVCLISDFYPGAVTVAWKAD
da-wt

PD-L1    QPKAAPSVTLFPPSSEELQANKATLVCLISDFYPGAVTVAWKAD

Lamb-    GSPVKAGVETTKPSKQSNNKYAASSYLSLTPEQWKSHRSYSCQV
da-wt

PD-L1    SSPVKAGVETTTPSKQSNNKYAAESELSLTPEQWKSHRSYSCQV

Lambda   THEGSTVEKTVAPTECS             (SEQ ID NO: 45)

PD-L1    THEGSTVEKTVAPAECS             (SEQ ID NO: 46)
```

The CL region of the anti-PD-1 portion of the antibody is preferably a human kappa subtype. The CL region of the anti-PD-1 portion of the antibodies of the present invention is preferably a human kappa variant comprising amino acid substitutions at positions 131, 133, and 176 in EU numbering.

Alignment of the Amino Acid Sequences of Wild-Type Human Kappa and the Constant Regions of the Light Chain of Antibodies Against PD-1 (Preferred Modifications are Underlined).

```
Kappa-   RTVAAPSVFIFPPSDEQLKSGTASVVCLLNNFYPREAKVQWKVDN
wt

PD-1     RTVAAPSVFIFPPSDEQLKSGTARVGCLLNNFYPREAKVQWKVDN

Kappa-   ALQSGNSQESVTEQDSKDSTYSLSSTLTLSKADYEKHKVYACEVT
wt

PD-1     ALQSGNSQESVTEQDSKDSTYSLRSTLTLSKADYEKHKVYACEVT

Kappa-   HQGLSSPVTKSFNRGEC             (SEQ ID NO: 47)
wt

PD-1     HQGLSSPVTKSFNRGEC             (SEQ ID NO: 48)
```

In certain antibodies of the present invention, heavy chain heterodimeric pairing mutations yield a CH3 thermal stability greater than 78° C.

When expressed in certain biological systems, antibodies having Fc sequences are glycosylated in the Fc region. Typically, glycosylation occurs in the Fc region of the antibody at a highly conserved N-glycosylation site. N-glycans typically attach to asparagine. Antibodies may be glycosylated at other positions as well.

Preferably, antibodies of the present invention contain an Fc portion variant which is derived from human IgG1. IgG1 is well known to bind to Fc-gamma receptor family (FcγR) as well as C1q. Interaction with these receptors can induce antibody-dependent cell cytotoxicity (ADCC) and complement-dependent cytotoxicity (CDC). Therefore, certain amino acid substitutions are introduced into human IgG1 Fc region for antibodies of the present invention to ablate immune effector functions. Mutations in the CH2 region of the antibody heavy chains may include positions 234, 235, and 265 in EU numbering to reduce or eliminate immune effector functions as shown in FIG. 1.

An isolated DNA encoding a HCVR region can be converted to a full-length heavy chain gene by operably linking the HCVR-encoding DNA to another DNA molecule encoding a heavy chain constant region or a variant thereof. The sequences of human, as well as other mammalian, heavy chain constant region genes are known in the art. DNA fragments encompassing these regions can be obtained e.g., by standard PCR amplification. Preferably, for antibodies of the present invention, the heavy chain constant regions of the heavy chains are variants of human IgG1.

An isolated DNA encoding a LCVR region may be converted to a full-length light chain gene by operably linking the LCVR-encoding DNA to another DNA molecule encoding a light chain constant region or a variant thereof. The sequences of human, as well as other mammalian, light chain constant region genes are known in the art. DNA fragments encompassing these regions can be obtained by standard PCR amplification. The light chain constant region can be a kappa or lambda constant region. Preferably, for antibodies of the present invention, the light chain constant region of the anti-PD-L1 portion of the antibody is a variant of lambda light chain and the light chain constant region of the anti-PD-1 portion of the antibody is a variant of kappa light chain.

The polynucleotides of the present invention may be expressed in a host cell after the sequences have been operably linked to an expression control sequence. The expression vectors are typically replicable in the host organisms either as episomes or as an integral part of the host chromosomal DNA. Commonly, expression vectors will contain selection markers, e.g., tetracycline, neomycin, glutamine synthetase, and dihydrofolate reductase, to permit detection of those cells transformed with the desired DNA sequences.

The antibody of the present invention may readily be produced in mammalian cells such as CHO, NS0, HEK293 or COS cells. The host cells are cultured using techniques well known in the art.

The vectors containing the polynucleotide sequences of interest (e.g., the polynucleotides encoding the polypeptides of the antibody and expression control sequences) can be transferred into the host cell by well-known methods, which vary depending on the type of cellular host.

Various methods of protein purification may be employed and such methods are known in the art and described, for example, in Deutscher, *Methods in Enzymology* 182: 83-89 (1990) and Scopes, *Protein Purification: Principles and Practice*, 3rd Edition, Springer, NY (1994).

In another embodiment of the present invention, the antibody, or the nucleic acids encoding the same, is provided in isolated form. As used herein, the term "isolated" refers to a protein, peptide, or nucleic acid which is free or substantially free from any other macromolecular species found in a cellular environment. "Substantially free" as used herein means the protein, peptide, or nucleic acid of interest comprises more than 80% (on a molar basis) of the macromolecular species present, preferably more than 90%, and more preferably more than 95%.

The antibody of the present invention, or pharmaceutical compositions comprising the same, may be administered by parenteral routes (e.g., subcutaneous and intravenous). An antibody of the present invention may be administered to a patient alone with pharmaceutically acceptable carriers, diluents, or excipients in single or multiple doses. Pharmaceutical compositions of the present invention can be prepared by methods well known in the art (e.g., *Remington: The Science and Practice of Pharmacy*, 22$^{nd}$ ed. (2012), A. Loyd et al., Pharmaceutical Press) and comprise an antibody, as disclosed herein, and one or more pharmaceutically acceptable carriers, diluents, or excipients.

The term "treating" (or "treat" or "treatment") refers to slowing, interrupting, arresting, alleviating, stopping, reducing, or reversing the progression or severity of an existing symptom, disorder, condition, or disease.

"Binds" as used herein in reference to the affinity of an antibody for human PD-L1 (SEQ ID NO: 1), human PD-1 (SEQ ID NO: 2), or both is intended to mean, unless indicated otherwise, a $K_D$ of less than about $1\times10^{-6}$ M, preferably, less than about $1\times10^{-9}$ M as determined by common methods known in the art, including by use of a surface plasmon resonance (SPR) biosensor at 37° C. essentially as described herein.

"Effective amount" means the amount of an antibody of the present invention or pharmaceutical composition comprising an antibody of the present invention that will elicit the biological or medical response of or desired therapeutic effect on a tissue, system, animal, mammal or human that is being sought by the researcher, medical doctor, or other clinician. An effective amount of the antibody may vary according to factors such as the disease state, age, sex, and weight of the individual, and the ability of the antibody to elicit a desired response in the individual. An effective amount is also one in which any toxic or detrimental effect of the antibody is outweighed by the therapeutically beneficial effects.

This invention is further illustrated by the following non-limiting Examples.

Example 1: Antibody Expression and Purification

The polypeptides of the variable regions of the heavy chain and light chain, the complete heavy chain and light chain amino acid sequences of Antibodies v3.2, v3.0 and v13844, and the nucleotide sequences encoding the same, are listed below in the section entitled "Amino Acid and Nucleotide Sequences." In addition, the SEQ ID NOs of the amino acid sequences of the light chain, heavy chain, light chain variable region, and heavy chain variable region of Antibodies v3.2, v3.0 and v13844 are shown in Table 1(a) below. Furthermore, the SEQ ID NOs for the amino acid sequences of the CDRs of the PD-L1 and PD-1 binding variable regions of Antibodies v3.2, v3.0 and v13844 are shown in Table 1(b) and Table 1(c), respectively.

The antibodies of the present invention, including, but not limited to, Antibodies v3.2, v3.0 and v13844, can be made and purified essentially as follows. An appropriate host cell, such as CHO, can be either transiently or stably transfected with an expression system for secreting antibodies using a quad vector (i.e., a single vector encoding for the expression of the two light chains and the two heavy chains), dual vectors (i.e., two vectors, which together encode the two different light chains and the two different heavy chains), or four single vectors (two of which encode a different light chain and two of which encode a different heavy chain). Media, into which the antibody has been secreted, may be purified using any of many commonly-used techniques. For example, the medium may be applied to a Mab Select column (GE Healthcare), or KappaSelect column (GE Healthcare) for Fab fragment, that has been equilibrated with a compatible buffer, such as phosphate buffered saline (pH 7.4). The column may be washed to remove nonspecific binding components. The bound antibody may be eluted, for example, by pH gradient (such as 20 mM Tris buffer pH 7 to 10 mM sodium citrate buffer pH 3.0, or phosphate buffered saline pH 7.4 to 100 mM glycine buffer pH 3.0). Antibody fractions may be detected, such as by SDS-PAGE, and then may be pooled. Soluble aggregate and multimers may be effectively removed by common techniques, including size exclusion, hydrophobic interaction, ion exchange, multimodal, or hydroxyapatite chromatography. The antibody may be concentrated and/or sterile filtered using common techniques. The product may be immediately frozen at −70° C. or may be lyophilized.

TABLES 1(a)-(c)

SEQ ID Nos for Checkpoint Inhibitor Bispecific Antibody (BsAb) Sequences

1(a)

| | Antibody v3.2 | Antibody v3.0 | Antibody v13844 |
|---|---|---|---|
| HCVR - anti-PD-L1 | 3 | 3 | 3 |
| HCVR - anti-PD-1 | 6 | 7 | 7 |
| LCVR - anti-PD-L1 | 4 | 4 | 4 |
| LCVR - anti-PD-1 | 8 | 8 | 8 |
| Heavy chain 1 - anti-PD-L1 | 49 | 49 | 29 |
| Heavy chain 2 - anti-PD-1 | 31 | 32 | 33 |
| Light chain 1 - anti-PD-L1 | 30 | 30 | 30 |
| Light chain 2 - anti-PD-1 | 34 | 34 | 34 |

1(b)

| Anti-PD-L1 | CDR1 | CDR2 | CDR3 |
|---|---|---|---|
| HC | KASGGTFSSYAIS (SEQ ID NO: 16) | GIIPIFGTANYAQKFQG (SEQ ID NO: 17) | ARSPDYSPYYYYGMDV (SEQ ID NO: 18) |
| LC | SGSSSNIGSNTVN (SEQ ID NO: 19) | YGNSNRPS (SEQ ID NO: 20) | QSYDSSLSGSV (SEQ ID NO: 21) |

1(c)

| | CDR1 | CDR2 | CDR3 |
|---|---|---|---|
| HC | KASGGTFSSYAIS (SEQ ID NO: 22) | LIIPSFDTAGYAQKFQG (SEQ ID NO: 23) or LIIPMFDTAGYAQKFQG (SEQ ID NO: 24) | ARAEHSSTGTFDY (SEQ ID NO: 25) |
| LC | RASQGISSWLA (SEQ ID NO: 26) | SAASSLQS (SEQ ID NO: 27) | QQANHLPFT (SEQ ID NO: 28) |

Example 2: Binding to Both Human PD-L1 and PD-1 as Measured by ELISA

The ability for antibodies of the present invention to bind both human PD-L1 and human PD-1 may be measured in a sandwich ELISA assay. For the PD-1 binding assay, a 96-well plate (Nunc) may be coated with human PD-1-Fc (R&D Systems, cat. #1086-PD) overnight at 4° C. Wells may be blocked for 2 hours with blocking buffer (PBS containing 5% nonfat dry milk). Wells may be washed three times with PBS containing 0.1% Tween-20. Anti-PD-1 antibody or control IgG (100 µl) may then be added and then the plate may be incubated at room temperature for 1 hour. After washing, the plate may be incubated with 100 µl of goat anti-human IgG F(ab')2-HRP conjugate (Jackson Immuno Resaerch, cat. #109-035-097) at room temperature for 1 hour. The plate may be washed and then may be incubated with 100 µl of 3,3', 5,5'-tetra-methylbenzidine. Absorbance at 450 nm may be read on a microplate reader. The half maximal effective concentration (EC50) may be calculated using GraphPad prism 6 software.

For the PD-L1 binding assay, a similar procedure may be applied, except that the 96-well plate (Nunc) may be coated with human PD-L1-Fc (R&D Systems, cat#156-B7) overnight at 4° C.

In experiments performed essentially as described above in this Example 2, Antibody v3.2 binds to human PD-1 with an EC50 of 0.0802 nM. In comparison, the binding affinity of the parent PD-1 antibody (as IgG4-PAA homodimer) is 0.1318 nM. Antibody v3.2 binds to human PD-L1 with an EC50 of 0.4554 nM. In comparison, the binding affinity of the parent PD-L1 antibody (as IgG1-EN homodimer) is 0.4702 nM.

Example 3: Bridging PD-1 Expressing Cells with PD-L1 Expressing Cells

The ability for antibodies of the present invention to bridge PD-1 and PD-L1 expressing cells was determined by flow cytometry analysis using transfected CHO cells expressing either PD-1 or PD-L1. Briefly stated, CHO-PD1 and CHOK1-PDL1 over expressing cells may be differentially labeled with CFSE (carboxyfluorescein diacetate succinimidyl ester) (BD Horizon) or Cell Tracker Deep Red (CTDR/Thermo). CHO-PD1 and CHOK1-PDL1 cells are separately incubated for 2 hours with a test antibody, such as Antibody v3.2 (on ice in PBS+1% BSA+0.09% sodium azide). Unbound antibodies may be removed by washing (2× with 200 µl PBS+1% BSA+0.09% sodium azide). CHOK1-PDL1 cells are incubated 2 hours with 45 µg/ml of the parent PD-L1 antibody or hIgG1 control on ice in PBS+1% BSA+ 0.09% sodium azide. CHO-PD1 cells are incubated 2 hours with 45 µg/ml of the parent of PD-1 antibody or huIgG4-PAA on ice in PBS+1% BSA+0.09% sodium azide. CHO-PD1/Antibody v3.2 cells are mixed with CHOK1-PDL1+ the parent PD-L1 antibody or hIgG1 at final concentration of 22.5 ug/ml. CHOK1-PDL1/Antibody v3.2 cells may be mixed with CHO-PD1+ the parent of the PD-1 antibody or huIgG4-PAA at a final concentration of 22.5 µg/ml. After an approximately 72 hour incubation (at 4° C.) cells may be measured on Fortessa X20 (with HTS sampler) in channels suitable for CFSE and CTDR. Using flowJo® software (FlowJo, LLC, Ashland, Oreg.), double positive events (CFSE+/CTDR+) may be gated and % of total events may be calculated and reported (for 2 replicate wells). Fits and statistics may be generated with Graphpad Prism using nonlinear regression (variable slope, 4 parameters).

In experiments performed essentially as described above in this Example 3, PD-1/PD-L1 bispecific antibodies mediate cell bridging which may be detected as double positive events by flow cytometry. Binding of Antibody v3.2 to CHO-PD1 or CHOK1-PDL1 cells (with subsequent removal of unbound) and then mixing with CHOK1-PDL1 or CHO-PD1 cells, respectively, caused a dose dependent increase in double positive events relative to background (up to 4-fold increase compared to buffer only). This increase in double positive events is blocked by the addition of excess competing PD-L1 and/or PD-1 mAbs at high concentration but not by matched non-specific IgG control, demonstrating specificity and dependence on target antigen expression.

Example 4: Blocking the Interactions of PD-L1 with PD-L2, PD-L1 with CD80 and PD-L2 with PD-1

A PD-L1/PD-1 blocking assay can be performed, by mixing varying amounts of anti-PD-1 antibody or control IgG with a fixed amount of biotinylated PD-1-Fc fusion protein (100 ng/mL) and incubating at room temperature for about 1 hour. Afterwards, the mixture may be transferred to 96-well plates pre-coated with PD-L1-Fc (100 ng/well) or PD-L2-Fc (100 ng/well) and then incubated at room temperature for approximately another 1 hour. After washing, streptavidin HRP conjugate may be added, and the absorbance at 450 nm may be read. IC50 represents the antibody concentration required for 50% inhibition of PD-1 binding to PD-L1 or binding to PD-L2.

Similarly, a PD-L1/B7-1 blocking assay may be performed by using plates coated with 1 µg/ml B7-1-Fc (R&D Systems, cat #140-B1-100). The antibody concentration required for 50% inhibition of PD-L1 binding to B7-1 (IC50) is calculated using GraphPad prism 6 software.

In experiments performed essentially as described above in this Example 4, Antibody v3.2 appeared to block the interaction between PD-1 receptor and PD-L1 ligand at intermediate and higher concentration and seems to bridge the receptor and the ligand with the dual binding at lower and intermediate concentration, with stronger affinities than the natural ligand-receptor interaction. Furthermore, Antibody v3.2 appeared to block the interaction of PD-L1 with B7-1 with an IC50 of 0.75 nM and the interaction of PD-L2 with PD-1 with an IC50 of 2.27 nM.

Example 5: In Vitro Functional Analysis of Antibodies in Mixed Leukocyte Reaction (MLR)

CD14+ monocytes may be isolated from frozen human PBMC obtained from a healthy donor (AllCells cat. #PB005F) with MACS beads (Miltenyi, cat. #130-091-153). Immature dendritic cells (DC) may be generated by culturing these monocytes in 12 ml complete RPMI-1640 medium in the presence of 1000 IU/ml hGM-CSF and 500 IU/ml hIL-4 for 4 days. CD4+ T cells may be purified from fresh human PBMC of a different healthy donor (AllCells cat. #PB002) by negative selection (Miltenyi 130-096-533). Then, the two types of cells may be mixed in individual wells of a 96-well plate with 100 µl complete AIM-V medium containing $5 \times 10^4$ CD4+ T cells and $4 \times 10^3$ immature DC per well (E:T=12.5:1). 100 µl complete AIM-V medium may be added containing human IgG1-EN, the parental anti-PD-1 antibody, the parental anti-PD-1 antibody, combinations of the parent antibodies, or Antibody v3.2 in 8 replicates (serially diluted by 3:1 from 32 nM), respectively). After incubation for 72 hours at 37° C. at 5% $CO_2$, supernatants may be harvested and then measured for human IFN-γ and IL-2 with ELISA kits (R&D cat #SIF50) and (R&D cat #S2050).

In experiments performed essentially as described above in this Example 5, addition of Antibody v3.2 to co-cultures of allogeneic CD4+ T cells and DC resulted in increased production of IFN-γ by responding CD4 T cell lymphocytes with an EC50 of 0.005 nM, compared to 0.026 nM, 0.029 nM and 0.115 nM for the parental PD-L1 Ab, the parental PD-1 Ab and a combination of the two, respectively. Similarly, Antibody v3.2 also increased production of IL-2 in the co-culture with an EC50 of 0.011 nM, compared to PD-L1 Ab, PD-1 Ab and PD-L1 Ab+PD-1 Ab combination (0.034 nM, 0.023 nM and 0.046 nM, respectively). The results indicate that Antibody v3.2 is superior in its ability to enhance T cell activation in vitro to the parental PD-L1 Ab alone, the parental PD-1 Ab alone or a combination thereof.

Example 6: Reinvigorating T Cells

PD-L1 positive human T-activator CHOK1 cells (Promega part #CS187108) and PD-L1 negative human T-activator CHOK1 cells (Promega part #CS187110) may be obtained from Promega. PD-L1/PD-L2 double positive human T-activator CHOK1 cells may be established by transfecting PD-L1 positive human T-activator CHOK1 cells with a vector encoding full-length PD-L2. These cells may be plated in a 96-well white opaque tissue culture plate at 40,000 cells per well in 100 µL medium (10% FBS F-12, 0.2 mg/ml Hygromycin-B and 0.2 mg/ml G418) and incubated overnight at 37° C. with 5% $CO_2$. Media may be removed from the assay plates on the following day and serially diluted test and control antibodies in assay buffer (2% FBS RPMI) may be added at 40 µl per well. GloResponse NFAT-luc2/PD1 Jurkat cells (Promega part #CS187102) may be resuspended in assay buffer at a concentration of $1.25 \times 10^6$/mL and added to the plate at 40 µl per well. After 6 hours of induction, assay plates may be removed from the incubator and equilibrated at room temperature for 5 to 10 minutes. Bio-Glo™ Reagent (Promega G7941) may be prepared according to the manufacturer's instructions and added at 80 µl per well. Then the plates may be incubated 5 to 10 minutes at room temperature. Luminescence may be measured in a plate reader and data may be analyzed using GraphPad Prism 7.

In a PD-1/NFAT Reporter Jurkat T cell assay performed essentially as described above in this Example 6, PD-L1 positive human T cell activator CHO cells were observed to suppress T cell activation. PD-1 Ab or PD-L1 Ab re-activated T cells by reversing PD-L1-PD-1 mediated suppression. However, Antibody v3.2 appeared superior (EC50

0.12 nM) to either the parental PD-L1 Ab alone (1.92 nM), the parental PD-1 Ab alone (1.01 nM), or combination of the parental PD-1 Ab and the parental PD-L1 Ab (0.796 nM) in its ability to reinvigorate T cells. When PD-L1/PD-L2 double positive human T cell activator CHO cells were used in this system, activation of PD-1 positive reporter T cells was also suppressed. The parental PD-1 Ab but not the parental PD-L1 Ab was able to re-activated T cells. However, Antibody v3.2 is superior (EC50 0.181 nM) to either the parental PD-1 Ab alone (0.946 nM), or a combination of the parental PD-1 Ab and the parental PD-L1 Ab (1.251 nM) in its ability to reinvigorate T cells.

Example 7: In Vivo Efficacy Assays

The efficacy of the antibodies of the present invention may be tested in xenograft models in immunodeficient mice reconstituted with human immune cells to assess the ability to delay or destroy established tumors in the model through enhancement of T-cell response to allo-antigens. All animal in studies are approved by the Institutional Animal Care and Use Committee and performed in accordance with current regulations and standards of the United States Department of Agriculture and the National Institute of Health.

Part A: NCI-11292 Human NSCLC Xenograft Model

NOD scid gamma (NSG) mice from Jackson Laboratories (7 weeks of age, female, in groups of 7-8 mice) are implanted into the flank subcutaneously with either $2 \times 10^6$ NCI-H292 cells, or a mixture of $2 \times 10^6$ NCI-H292 cells and $1 \times 10^6$ human freshly isolated PBMCs in HBSS (0.2 ml total volume). Starting on Day 1, mice are treated with an intraperitoneal injection of either human IgG1-EN (control), the parental anti-PD-L1 antibody (0.25 mg/kg), or the parental anti-PD-1 antibody (0.25 mg/kg), or combination of the parental antibodies (0.25 mg/kg each), or Antibody v3.0, v3.2 or v13844 (0.5 mg/kg) once weekly for three doses. Animal well-being and behavior, including grooming and ambulation are monitored at least twice per week. Body weight and tumor volume are measured twice a week.

In experiments performed essentially as described above in Part A of Example 7, Antibodies v3.0, v3.2 and v13844 dosed at 10 mg/kg were well tolerated and safe as monitored by body weight and clinical observations. In mice implanted with mixture of NCI-H292 tumor cells and PBMC, treatment with anti-PD-L1 or anti-PD-1 antibody, or combination of anti-PD-L1 and anti-PD-1 antibodies at 10 mg/kg each all delayed tumor growth as compared to treatment with the control molecule, human IgG1-EN. In mice implanted with mixture of NCI-H292 tumor cells and PBMC, treatment with PD-1/PD-L1 bispecific Ab (v13844, v3.0 or v3.2) at 10 mg/kg qw were all more efficacious with a complete regression (CR) in 7/8, 5/8 and 5/8, respectively, than the combination therapy (parental PD-L1 antibody+ parental PD-1 antibody) (CR in 2/8).

Part B: HCC827 Human NSCLC Xenograft Model

NSG mice from Jackson Laboratories (7 weeks of age, female, in groups of 8 mice) are implanted into the flank subcutaneously with $10 \times 10^6$ HCC827 cells in HBSS (0.2 ml total volume). Bulk human T cells isolated from whole blood (New York Blood Center) are expanded using Human T-Activator CD3/CD28 Dynabeads® for 10 days and cryopreserved. T cells are thawed, washed, counted, and infused intravenously ($3.5 \times 10^6$ T cells in 0.2 ml PBS per mouse) into HCC827 tumor-bearing mice on day 44 from implantation. Starting the next day, mice are treated with an intraperitoneal injection of human IgG1-EN (control), parental anti-PD-L1 antibody, parental anti-PD-1 antibody, or the combination of the parental anti-PD-L1 antibody and the parental anti-PD-1 antibody, at 2 mg/kg each, or Antibody v3.2 at three dose levels (0.02, 0.2 or 2 mg/kg), once weekly for 4 weeks. Mice are given a second infusion of expanded T cells ($2.5 \times 10^6$ T cells in 0.2 ml PBS per mouse) on Day 56. Animal well-being and behavior, including grooming and ambulation are monitored at least twice per week. Body weight and tumor volume are measured twice a week. Tumor volumes are measured once per week using electronic calipers as described in the SOP entitled: IM-Tumor Growth Measurement. Tumor volume is calculated using a formula: Tumor Volume (mm$^3$)=$\pi/6$*Length*Width$^2$.

In experiments performed essentially as described above in Part B of Example 7, Antibody v3.2 at all three dose levels (0.02, 0.2 or 2 mg/kg) shared similar anti-tumor response in the established HCC827 tumor model in the presence of expanded T cells. Moreover, Antibody v3.2 at 0.02 mg/kg delayed tumor growth more significantly than anti-PD-L1 Antibody (2 mg/kg, p=0.05), anti-PD-1 Antibody (2 mg/kg, p<0.001) and the combination of both agents (2 mg/kg each, p<0.001) on Day 69 post tumor cell implantation (see, Table 2).

TABLE 2

Tumor inhibition on Day 69 in HCC827 human NSCLC established tumor model

| Treatment Group | Tumor volume (in mm$^3$) on Day 69 (Mean ± SEM) | p value (vs. 0.02 mg/kg BsAb v3.2/T cells) |
| --- | --- | --- |
| 2 mg/kg Human IgG1-EN | 1572.4 ± 87.8 | <0.001 |
| 2 mg/kg Human IgG1-EN/T cells | 1062.2 ± 81.7 | <0.001 |
| 2 mg/kg Anti PD-L1 mAb/T cells | 968.7 ± 58.7 | 0.005 |
| 2 mg/kg Anti PD-1 mAb/T cells | 1275.0 ± 67.2 | <0.001 |
| 2 mg/kg Anti PD-L1 mAb + 2 mg/kg Anti PD-1 mAb/T cells | 1021.0 ± 58.9 | <0.001 |
| 0.02 mg/kg Antibody v3.2/T cells | 761.8 ± 33.3 | NA |
| 0.2 mg/kg Antibody v3.2/T cells | 759.8 ± 43.3 | 0.975 |
| 2 mg/kg Antibody v3.2/T cells | 721.3 ± 49.2 | 0.516 |

SEM: standard estimation of mean

Amino Acid and Nucleotide Sequences (human PD-L1)

SEQ ID NO: 1

MRIFAVFIFMTYWHLLNAFTVTVPKDLYVVEYGSNMTIECKFPVEKQLDLAALIVYWEME

DKNIIQFVHGEEDLKVQHSSYRQRARLLKDQLSLGNAALQITDVKLQDAGVYRCMISYGG

ADYKRITVKVNAPYNKINQRILVVDPVTSEHELTCQAEGYPKAEVIWTSSDHQVLSGKTT

TTNSKREEKLFNVTSTLRINTTTNEIFYCTFRRLDPEENHTAELVIPELPLAHPPNERTH

LVILGAILLCLGVALTFIFRLRKGRMMDVKKCGIQDTNSKKQSDTHLEET

-continued (human PD-1)
                                                      SEQ ID NO: 2
MQIPQAPWPVVWAVLQLGWRPGWFLDSPDRPWNPPTFSPALLVVTEGDNATFTCSFSNTS

ESFVLNWYRMSPSNQTDKLAAFPEDRSQPGQDCRFRVTQLPNGRDFHMSVVRARRNDSGT

YLCGAISLAPKAQIKESLRAELRVTERRAEVPTAHPSPSPRPAGQFQTLVVGVVGGLLGS

LVLLVWVLAVICSRAARGTIGARRTGQPLKEDPSAVPVFSVDYGELDFQWREKTPEPPVP

CVPEQTEYATIVFPSGMGTSSPARRGSADGPRSAQPLRPEDGHCSWPL (HCVR of PD-L1 Ab)
                                                      SEQ ID NO: 3
QVQLVQSGAEVKKPGSSVKVSCKASGGTFSSYAISWVRQAPGQGLEWMGGIIPIFGTANY

AQKFQGRVTITADKSTSTAYMELSSLRSEDTAVYYCARSPDYSPYYYYGMDVWGQGTTVT

VSS (LCVR of PD-L1 Ab)
                                                      SEQ ID NO: 4
QSVLTQPPSASGTPGQRVTISCSGSSSNIGSNTVNWYQQLPGTAPKLLIYGNSNRPSGVP

DRFSGSKSGTSASLAISGLQSEDEADYYCQSYDSSLSGSVFGGGIKLTVLG (HCVR of PD-1 Ab-Xaa)
                                                      SEQ ID NO: 5
QVQLVQSGAEVKKPGSSVKVSCKASGGTFSSYAISWVRQAPGQGLEWMGLIIPXaaFDTA

GYAQKFQGRVAITVDESTSTAYMELSSLRSEDTAVYYCARAEHSSTGTFDYWGQGTLVTV

SS
Xaa: M or S.

(HCVR of PD-1 Xaa-S)
                                                      SEQ ID NO: 6
QVQLVQSGAE VKKPGSSVKV SCKASGGTFS SYAISWVRQA PGQGLEWMGL

IIPSFDTAGY AQKFQGRVAI TVDESTSTAY MELSSLRSED TAVYYCARAE

HSSTGTFDYW GQGTLVTVSS (HCVR of PD-1 Xaa-M)
                                                      SEQ ID NO: 7
QVQLVQSGAE VKKPGSSVKV SCKASGGTFS SYAISWVRQA PGQGLEWMGL

IIPMFDTAGY AQKFQGRVAI TVDESTSTAY MELSSLRSED TAVYYCARAE

HSSTGTFDYW GQGTLVTVSS (LCVR of PD-1 Ab)
                                                      SEQ ID NO: 8
DIQMTQSPSSVSASVGDRVTITCRASQGISSWLAWYQQKPGKAPKLLISAASSLQSGVPS

RFSGSGSGTDFTLTISSLQPEDFATYYCQQANHLPFTFGGGTKVEIK (region from CH1 domain of PD-L1 Ab v3.2 and
v13844 HC)
                                                      SEQ ID NO: 9
SLKSV (region from CH2 domain of PD-L1 Ab HC)
                                                      SEQ ID NO: 10
AAGGPSVFLFPPKPKDTLMISRTPEVTCVVVS (region of CH3 domain of HC for PD-1 v13844 and
PD-L1 v3.2)
                                                      SEQ ID NO: 11
VYPPSRDELTKNQVSLTCLVKGFYPSDIAVEWESNGQPENNYKTTPPVLDSDGSFALV (region of CH3 domain of HC for PD-1 v3.2 and
PD-L1 v13844)
                                                      SEQ ID NO: 12
VLPPSRDELTKNQVSLLCLVKGFYPSDIAVEWESNGQPENNYLTW (region from CH1 domain of PD-1 Ab v3.2 and
PD-1 v13844 HC)
                                                      SEQ ID NO: 13
EAPSSKSTSGGTAALGCLVTDYFPEPVTVSWNSGALTSGV HTFPAVLE -continued (region from LC constant region of PD-L1 v3.2 and
v13844 Abs)
SEQ ID NO: 14
AAESELS (region from LC constant region of PD-1 v3.2 and
v13844 Ab)
SEQ ID NO: 15
RVGCLLNNFYPREAKVQWKVDNALQSGNSQESVTEQDSKDSTYSLR (HCDR1 of PD-L1 Ab)
SEQ ID NO: 16
KASGGTFSSYAIS (HCDR2 of PD-L1 Ab)
SEQ ID NO: 17
GIIPIFGTANYAQKFQG (HCDR3 of PD-L1 Ab)
SEQ ID NO: 18
ARSPDYSPYYYYGMDV (LCDR1 of PD-L1 Ab)
SEQ ID NO: 19
SGSSSNIGSNTVN (LCDR2 of PD-L1 Ab)
SEQ ID NO: 20
YGNSNRPS (LCDR3 of PD-L1 Ab)
SEQ ID NO: 21
QSYDSSLSGSV (HCDR1 of PD-1 Ab)
SEQ ID NO: 22
KASGGTFSSYAIS (HCDR2 of PD-1 Ab; v3.2)
SEQ ID NO: 23
LIIPSFDTAGYAQKFQG (HCDR2 of PD-1 Ab; v3.0)
SEQ ID NO: 24
LIIPMFDTAGYAQKFQG (HCDR3 of PD-1 Ab)
SEQ ID NO: 25
ARAEHSSTGTFDY (LCDR1 of PD-1 Ab)
SEQ ID NO: 26
RASQGISSWLA (LCDR2 of PD-1 Ab)
SEQ ID NO: 27
SAASSLQS (LCDR3 of PD-1 Ab)
SEQ ID NO: 28
QQANHLPFT (HC of PD-L1 Ab v13844)
SEQ ID NO: 29
QVQLVQSGAEVKKPGSSVKVSCKASGGTFSSYAISWVRQAPGQGLEWMGGIIPIFGTANY

AQKFQGRVTITADKSTSTAYMELSSLRSEDTAVYYCARSPDYSPYYYYGMDVWGQGTTVT

VSSASTKGPSVFPLAPSSKSTSGGTAALGCLVKDYFPEPVTVSWNSGALTSGVHTFPAVL

QSSGLYSLSSVVTVPSSSLGTQTYICNVNHKPSNTKVDKRVEPKSCDKTHTCPPCPAPEA

AGGPSVFLFPPKPKDTLMISRTPEVTCVVVSVSHEDPEVKFNWYVDGVEVHNAKTKPREE

QYNSTYRVVSVLTVLHQDWLNGKEYKCKVSNKALPAPIEKTISKAKGQPREPQVYVLPPS

RDELTKNQVSLLCLVKGFYPSDIAVEWESNGQPENNYLTWPPVLDSDGSFFLYSKLTVDK

SRWQQGNVFSCSVMHEALHNHYTQKSLSLSPGK

-continued (LC of PD-L1 Ab v3.2, v3.0 and v13844)
SEQ ID NO: 30
QSVLTQPPSASGTPGQRVTISCSGSSSNIGSNTVNWYQQLPGTAPKLLIYGNSNRPSGVP

DRFSGSKSGTSASLAISGLQSEDEADYYCQSYDSSLSGSVFGGGIKLTVLGQPKAAPSVT

LFPPSSEELQANKATLVCLISDFYPGAVTVAWKADSSPVKAGVETTTPSKQSNNKYAAES

ELSLTPEQWKSHRSYSCQVTHEGSTVEKTVAPAECS (HC of PD-1 Ab v3.2)
SEQ ID NO: 31
QVQLVQSGAE VKKPGSSVKV SCKASGGTFS SYAISWVRQA PGQGLEWMGL

IIPSFDTAGY AQKFQGRVAI TVDESTSTAY MELSSLRSED TAVYYCARAE

HSSTGTFDYW GQGTLVTVSS ASTKGPSVFP EAPSSKSTSG GTAALGCLVT

DYFPEPVTVS WNSGALTSGV HTFPAVLESS GLYSLSSVVT VPSSSLGTQT

YICNVNHKPS NTKVDKRVEP KSCDKTHTCP PCPAPEAAGG PSVFLFPPKP

KDTLMISRTP EVTCVVVSVS HEDPEVKFNW YVDGVEVHNA KTKPREEQYN

STYRVVSVLT VLHQDWLNGK EYKCKVSNKA LPAPIEKTIS KAKGQPREPQ

VYVLPPSRDE LTKNQVSLLC LVKGFYPSDI AVEWESNGQP ENNYLTWPPV

LDSDGSFFLY SKLTVDKSRW QQGNVFSCSV MHEALHNHYT QKSLSLSPGK (HC of PD-1 v3.0)
SEQ ID NO: 32
QVQLVQSGAE VKKPGSSVKV SCKASGGTFS SYAISWVRQA PGQGLEWMGL

IIPMFDTAGY AQKFQGRVAI TVDESTSTAY MELSSLRSED TAVYYCARAE

HSSTGTFDYW GQGTLVTVSS ASTKGPSVFP EAPSSKSTSG GTAALGCLVT

DYFPEPVTVS WNSGALTSGV HTFPAVLESS GLYSLSSVVT VPSSSLGTQT

YICNVNHKPS NTKVDKRVEP KSCDKTHTCP PCPAPEAAGG PSVFLFPPKP

KDTLMISRTP EVTCVVVSVS HEDPEVKFNW YVDGVEVHNA KTKPREEQYN

STYRVVSVLT VLHQDWLNGK EYKCKVSNKA LPAPIEKTIS KAKGQPREPQ

VYVLPPSRDE LTKNQVSLLC LVKGFYPSDI AVEWESNGQP ENNYLTWPPV

LDSDGSFFLY SKLTVDKSRW QQGNVFSCSV MHEALHNHYT QKSLSLSPGK (HC of PD-1 Ab v13844)
SEQ ID NO: 33
QVQLVQSGAE VKKPGSSVKV SCKASGGTFS SYAISWVRQA PGQGLEWMGL

IIPMFDTAGY AQKFQGRVAI TVDESTSTAY MELSSLRSED TAVYYCARAE

HSSTGTFDYW GQGTLVTVSS ASTKGPSVFP EAPSSKSTSG GTAALGCLVT

DYFPEPVTVS WNSGALTSGV HTFPAVLESS GLYSLSSVVT VPSSSLGTQT

YICNVNHKPS NTKVDKRVEP KSCDKTHTCP PCPAPEAAGG PSVFLFPPKP

KDTLMISRTP EVTCVVVSVS HEDPEVKFNW YVDGVEVHNA KTKPREEQYN

STYRVVSVLT VLHQDWLNGK EYKCKVSNKA LPAPIEKTIS KAKGQPREPQ

VYVYPPSRDE LTKNQVSLTC LVKGFYPSDI AVEWESNGQP ENNYKTTPPV

LDSDGSFALV SKLTVDKSRW QQGNVFSCSV MHEALHNHYT QKSLSLSPGK (LC of PD-1 Ab v3.2, v3.0 and v13844)
SEQ ID NO: 34
DIQMTQSPSS VSASVGDRVT ITCRASQGIS SWLAWYQQKP GKAPKLLISA

ASSLQSGVPS RFSGSGSGTD FTLTISSLQP EDFATYYCQQ ANHLPFTFGG

GTKVEIKRTV AAPSVFIFPP SDEQLKSGTA RVGCLLNNFY PREAKVQWKV

DNALQSGNSQ ESVTEQDSKD STYSLRSTLT LSKADYEKHK VYACEVTHQG

LSSPVTKSFN RGEC

-continued

DNA Sequence of PD-L1 LC

SEQ ID NO: 35

CAGTCCGTCC TGACTCAGCC ACCTTCCGCT AGCGGTACCC CCGGCCAGAG

AGTGACAATC TCATGCTCCG GTTCCAGCTC TAACATTGGC TCTAACACTG

TCAATTGGTA CCAGCAGCTG CCAGGAACCG CACCAAAGCT GCTGATCTAT

GGAAACTCAA ATAGGCCTAG CGGGGTGCCA GACCGGTTTA GCGGATCTAA

AAGTGGGACT TCAGCTTCCC TGGCAATTTC TGGACTGCAG AGTGAGGACG

AAGCTGATTA CTATTGCCAG TCCTACGATA GTTCACTGAG CGGTTCCGTG

TTCGGCGGAG GGATCAAGCT GACAGTCCTG GGCCAGCCCA AGGTGAGTTC

TAGAGGATCC ATCTGGGATA AGCATGCTGT TTTCTGTCTG TCCCTAACAT

GCCCTGTGAT TATCCGCAAA CAACACACCC AAGGGCAGAA CTTTGTTACT

TAAACACCAT CCTGTTTGCT TCTTTCCTCA GGCCGCTCCT TCCGTGACTC

TGTTTCCCCC TTCCAGCGAG GAACTGCAGG CCAATAAGGC CACCCTGGTG

TGCCTGATTA GCGACTTCTA TCCTGGAGCT GTGACAGTCG CATGGAAGGC

CGATTCTAGT CCAGTGAAAG CAGGGGTCGA GACCACAACT CCCTCCAAGC

AGAGCAACAA CAAGTACGCA GCCGAGTCTG AACTGAGTCT GACCCCAGAA

CAGTGGAAGT CCCACAGGAG TTATTCATGC CAGGTGACCC ATGAGGGCTC

CACAGTGGAG AAGACCGTGG CCCCTGCTGA GTGTAGC

DNA Sequence of PD-1 LC

SEQ ID NO: 36

GACATTCAGATGACCCAGAGCCCAAGCAGCGTGAGCGCCAGCGTCGGGGA

CCGAGTGACCATCACATGCAGGGCCAGCCAGGGTATTTCTAGTTGGCTGG

CTTGGTACCAGCAGAAGCCAGGCAAAGCACCCAAGCTGCTGATCTCCGCC

GCTTCAAGCCTGCAGTCCGGAGTGCCCTCTCGATTCTCTGGTAGTGGCTC

AGGAACAGACTTTACTCTGACCATTTCCTCTCTGCAGCCTGAGGATTTCG

CTACTTACTATTGCCAGCAGGCAAACCACCTGCCATTCACCTTTGGCGGA

GGGACAAAAGTGGAGATCAAGAGAACCGTCGCGGCGCCCAGTGTCTTCAT

TTTTCCCCCTAGCGACGAACAGCTGAAGTCTGGGACAGCCAGAGTGGGCT

GTCTGCTGAACAACTTCTACCCTAGAGAGGCTAAAGTGCAGTGGAAGGTC

GATAACGCACTGCAGTCCGGAAATTCTCAGGAGAGTGTGACTGAACAGGA

CTCAAAAGATAGCACCTATTCCCTGAGAAGCACACTGACTCTGAGCAAGG

CCGACTACGAGAAGCATAAAGTGTATGCTTGTGAAGTCACCCACCAGGGG

CTGAGTTCACCAGTCACAAAATCATTCAACAGAGGGGAGTGC

DNA Sequence of PD-L1 HC

SEQ ID NO: 37

CAGGTCCAGC TGGTGCAGAG CGGAGCCGAA GTGAAGAAAC CCGGTAGCAG

CGTCAAAGTG TCATGTAAAG CCTCAGGGGG AACATTCTCC AGCTACGCCA

TCTCCTGGGT GAGACAGGCT CCAGGACAGG GACTGGAGTG GATGGGAGGA

ATCATCCCTA TCTTCGGCAC CGCCAACTAC GCTCAGAAGT TCAGGGCCG

CGTGACCATC ACAGCCGACA AGAGCACCTC TACAGCTTAT ATGGAGCTGT

CTTCCCTGAG AAGCGAGGAT ACAGCCGTGT ACTATTGCGC TCGCTCCCCC

GACTACAGCC CTTACTATTA CTATGGCATG GACGTGTGGG GCCAGGGCAC

CACAGTGACC GTGAGCTCTG CTAGCACAAA GGGCCCATCC GTGTTCCCAC

-continued

```
TGGCTCCATC CAGCAAGTCC ACCAGCGGAG GAACAGCCGC TCTGGGCTGT

CTGGTGAAGG ACTATTTCCC AGAGCCAGTG ACCGTGTCCT GGAACAGCGG

CGCCCTGACC TCTGGAGTGC ACACATTTCC CGCTGTGCTG CAGTCTTCCG

GCCTGTACTC TCTGAAGTCC GTGGTGACCG TGCCTAGCTC TTCCCTGGGC

ACCCAGACAT ATATCTGCAA CGTGAATCAC AAGCCTTCCA ATACAAAGGT

GGACAAGAGG GTGGAGCCAA AGAGCTGTGA TAAGACCCAT ACATGCCCCC

CTTGTCCTGC TCCAGAGGCT GCTGGAGGAC CAAGCGTGTT CCTGTTTCCA

CCCAAGCCCA AGGACACCCT GATGATCTCT AGGACCCCTG AGGTGACATG

CGTGGTGGTG TCCGTGTCCC ACGAGGACCC AGAGGTGAAG TTTAACTGGT

ACGTGGATGG CGTGGAGGTG CATAATGCTA AGACCAAGCC TAGGGAGGAG

CAGTACAACA GCACCTATCG GGTGGTGTCT GTGCTGACAG TGCTGCATCA

GGATTGGCTG AACGGCAAGG AGTATAAGTG CAAGGTGTCT AATAAGGCCC

TGCCCGCTCC TATCGAGAAG ACCATCTCCA AGGCCAAGGG CCAGCCTAGG

GAGCCACAGG TGTACGTGCT GCCTCCAAGC CGGGACGAGC TGACAAAGAA

CCAGGTGTCT CTGCTGTGCC TGGTGAAGGG CTTCTATCCA TCTGATATCG

CTGTGGAGTG GGAGTCCAAT GGCCAGCCCG AGAACAATTA CCTGACCTGG

CCCCCTGTGC TGGACAGCGA TGGCTCTTTC TTTCTGTATT CCAAGCTGAC

AGTGGATAAG AGCCGGTGGC AGCAGGGCAA CGTGTTCTCC TGTTCTGTGA

TGCACGAGGC ACTGCACAAT CATTACACCC AGAAATCCCT GTCACTGAGC

CCCGGCAAG
```

DNA Sequence of PD-1 HC (v3.2)    SEQ ID NO: 38

```
CAGGTCCAGCTGGTGCAGAGCGGGGCAGAGGTCAAGAAACCCGGTAGCTC

CGTGAAGGTCAGCTGCAAGGCTTCCGGCGGAACCTTCTCTAGTTACGCCA

TCAGCTGGGTGAGACAGGCTCCTGGCCAGGGACTGGAATGGATGGGCCTG

ATCATTCCATCTTTTGATACCGCTGGCTACGCACAGAAGTTTCAGGGACG

GGTGGCAATTACAGTCGATGAGTCAACCAGCACAGCCTATATGGAGCTGT

CAAGCCTGCGGTCCGAAGACACTGCCGTGTACTATTGCGCAAGGGCCGAA

CACTCCTCTACTGGAACCTTCGATTACTGGGGGCAGGGTACCCTGGTGAC

AGTCAGTTCAGCCAGCACTAAGGGACCCAGCGTGTTTCCAGAGGCCCCCT

CTAGTAAATCCACTTCTGGAGGCACCGCTGCACTGGGCTGTCTGGTGACC

GATTACTTCCCAGAGCCCGTCACAGTGAGCTGGAACTCCGGGGCCCTGAC

CAGCGGAGTCCATACATTTCCTGCTGTGCTGGAGTCAAGCGGGCTGTACT

CCCTGTCCTCTGTGGTCACCGTGCCAAGTTCAAGCCTGGGAACTCAGACC

TATATCTGCAACGTGAATCACAAGCCTTCAAATACAAAAGTTGACAAACG

TGTGGAACCCAAGAGTTGTGATAAAACCCATACATGCCCCCCTTGTCCGG

CGCCAGAGGCTGCAGGAGGACCAAGCGTGTTCCTGTTTCCACCCAAGCCT

AAAGACACACTGATGATTTCCCGAACCCCCGAAGTCACATGCGTGGTCGT

GTCTGTGAGTCACGAGGACCCTGAAGTCAAGTTCAACTGGTACGTGGATG

GCGTCGAGGTGCATAATGCCAAGACTAAACCTAGGGAGGAACAGTACAAC

TCAACCTATCGCGTCGTGAGCGTCCTGACAGTGCTGCACCAGGATTGGCT

GAACGGCAAAGAATATAAGTGCAAAGTGAGCAATAAGGCCCTGCCCGCTC
```

```
CTATCGAGAAAACCATTTCCAAGGCTAAAGGGCAGCCTCGCGAACCACAG

GTCTACGTGCTGCCTCCATCCCGGGACGAGCTGACAAAGAACCAGGTCTC

TCTGCTGTGCCTGGTGAAAGGCTTCTATCCATCAGATATTGCTGTGGAGT

GGGAAAGCAATGGGCAGCCCGAGAACAATTACCTGACTTGGCCCCCTGTG

CTGGACTCTGATGGGAGTTTCTTTCTGTATTCTAAGCTGACCGTGGATAA

AAGTAGGTGGCAGCAGGGAAATGTCTTTAGTTGTTCAGTGATGCATGAAG

CCCTGCATAACCACTACACCCAGAAAAGCCTGTCCCTGTCCCCCGGAAAA
```

DNA Sequence of PD-1 HC (v13844)                SEQ ID NO: 39

```
CAGGTCCAGCTGGTGCAGAGCGGGGCAGAGGTCAAGAAACCCGGTAGCTC

CGTGAAGGTCAGCTGCAAGGCTTCCGGCGGAACCTTCTCTAGTTACGCCA

TCAGCTGGGTGAGACAGGCTCCTGGCCAGGGACTGGAATGGATGGGCCTG

ATCATTCCAATGTTCGACACCGCTGGCTACGCACAGAAGTTTCAGGGACG

GGTGGCAATTACAGTCGATGAGTCAACCAGCACAGCCTATATGGAGCTGT

CAAGCCTGCGGTCCGAAGACACTGCCGTGTACTATTGCGCAAGGGCCGAA

CACTCCTCTACTGGAACCTTCGATTACTGGGGGCAGGGTACCCTGGTGAC

AGTCAGTTCAGCCAGCACTAAGGGACCCAGCGTGTTTCCAGAGGCCCCCT

CTAGTAAATCCACTTCTGGAGGCACCGCTGCACTGGGCTGTCTGGTGACC

GATTACTTCCCAGAGCCCGTCACAGTGAGCTGGAACTCCGGGGCCCTGAC

CAGCGGAGTCCATACATTTCCTGCTGTGCTGGAGTCAAGCGGGCTGTACT

CCCTGTCCTCTGTGGTCACCGTGCCAAGTTCAAGCCTGGGAACTCAGACC

TATATCTGCAACGTGAATCACAAGCCTTCAAATACAAAAGTTGACAAACG

TGTGGAACCCAAGAGTTGTGATAAAACCCATACATGCCCCCCTTGTCCGG

CGCCAGAGGCTGCAGGAGGACCAAGCGTGTTCCTGTTTCCACCCAAGCCT

AAAGACACACTGATGATTTCCCGAACCCCCGAAGTCACATGCGTGGTCGT

GTCTGTGAGTCACGAGGACCCTGAAGTCAAGTTCAACTGGTACGTGGATG

GCGTCGAGGTGCATAATGCCAAGACTAAACCTAGGGAGGAACAGTACAAC

TCAACCTATCGCGTCGTGAGCGTCCTGACAGTGCTGCACCAGGATTGGCT

GAACGGCAAAGAATATAAGTGCAAAGTGAGCAATAAGGCCCTGCCCGCTC

CTATCGAGAAACCATTTCCAAGGCTAAAGGGCAGCCTCGCGAACCACAG

GTCTACGTGTATCCTCCAAGCCGGGACGAGCTGACAAAGAACCAGGTCTC

CCTGACTTGTCTGGTGAAAGGGTTTTACCCTAGTGATATCGCTGTGGAGT

GGGAATCAAATGGACAGCCAGAGAACAATTATAAGACTACCCCCCCTGTG

CTGGACAGTGATGGGTCATTCGCACTGGTCTCCAAGCTGACAGTGGACAA

ATCTCGGTGGCAGCAGGGAAATGTCTTTTCATGTAGCGTGATGCATGAAG

CACTGCACAACCATTACACCCAGAAGTCACTGTCACTGTCACCAGGAAAA
```

IgG1 CH wt                                     SEQ ID NO: 40

```
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK
```

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK v3.2 PD-L1 CH                                           SEQ ID NO: 41

ASTKGPSVFPLAPSSKSTSGGTAALGCLVKDYFPEPVTVSWNSGALTSGV

HTFPAVLQSSGLYSLKSVVTVPSSSLGTQTYICNVNHKPSNTKVDKRVEP

KSCDKTHTCPPCPAPEAAGGPSVFLFPPKPKDTLMISRTPEVTCVVVSVS

HEDPEVKFNWYVDGVEVHNAKTKPREEQYNSTYRVVSVLTVLHQDWLNGK

EYKCKVSNKALPAPIEKTISKAKGQPREPQVYVYPPSRDELTKNQVSLTC

LVKGFYPSDIAVEWESNGQPENNYKTTPPVLDSDGSFALVSKLTVDKSRW

QQGNVFSCSVMHEALHNHYTQKSLSLSPGK v13844 PD-1 CH                                          SEQ ID NO: 42

ASTKGPSVFPEAPSSKSTSGGTAALGCLVTDYFPEPVTVSWNSGALTSGV

HTFPAVLESSGLYSLSSVVTVPSSSLGTQTYICNVNHKPSNTKVDKRVEP

KSCDKTHTCPPCPAPEAAGGPSVFLFPPKPKDTLMISRTPEVTCVVVSVS

HEDPEVKFNWYVDGVEVHNAKTKPREEQYNSTYRVVSVLTVLHQDWLNGK

EYKCKVSNKALPAPIEKTISKAKGQPREPQVYVYPPSRDELTKNQVSLTC

LVKGFYPSDIAVEWESNGQPENNYKTTPPVLDSDGSFALVSKLTVDKSRW

QQGNVFSCSVMHEALHNHYTQKSLSLSPGK v3.2 PD-1 CH                                            SEQ ID NO: 43

ASTKGPSVFPEAPSSKSISGGTAALGCLVTDYFPEPVTVSWNSGALTSGV

HTFPAVLESSGLYSLSSVVTVPSSSLGTQTYICNVNHKPSNTKVDKRVEP

KSCDKTHTCPPCPAPEAAGGPSVFLFPPKPKDTLMISRTPEVTCVVVSVS

HEDPEVKFNWYVDGVEVHNAKTKPREEQYNSTYRVVSVLTVLHQDWLNGK

EYKCKVSNKALPAPIEKTISKAKGQPREPQVYVLPPSRDELTKNQVSLLC

LVKGFYPSDIAVEWESNGQPENNYLTWPPVLDSDGSFFLYSKLTVDKSRW

QQGNVFSCSVMHEALHNHYTQKSLSLSPGK v13844 PD-L1 CH                                         SEQ ID NO: 44

ASTKGPSVFPLAPSSKSTSGGTAALGCLVKDYFPEPVTVSWNSGALTSGV

HTFPAVLQSSGLYSLKSVVTVPSSSLGTQTYICNVNHKPSNTKVDKRVEP

KSCDKTHTCPPCPAPEAAGGPSVFLFPPKPKDTLMISRTPEVTCVVVSVS

HEDPEVKFNWYVDGVEVHNAKTKPREEQYNSTYRVVSVLTVLHQDWLNGK

EYKCKVSNKALPAPIEKTISKAKGQPREPQVYVLPPSRDELTKNQVSLLC

LVKGFYPSDIAVEWESNGQPENNYLTWPPVLDSDGSFFLYSKLTVDKSRW

QQGNVFSCSVMHEALHNHYTQKSLSLSPGK

CL Lambda-wildtype                                      SEQ ID NO: 45

QPKANPTVTLFPPSSEELQANKATLVCLISDFYPGAVTVAWKADGSPVKAGVETTKPSKQ

SNNKYAASSYLSLTPEQWKSHRSYSCQVTHEGSTVEKTVAPTECS

CL PD-L1                                                SEQ ID NO: 46

QPKAAPSVTLFPPSSEELQANKATLVCLISDFYPGAVTVAWKADSSPVKAGVETTTPSKQ

SNNKYAAESELSLTPEQWKSHRSYSCQVTHEGSTVEKTVAPAECS

CL Kappa-wildtype
SEQ ID NO: 47
RTVAAPSVFIFPPSDEQLKSGTASVVCLLNNFYPREAKVQWKVDNALQSGNSQESVTEQD
SKDSTYSLSSTLTLSKADYEKHKVYACEVTHQGLSSPVTKSFNRGEC CL Kappa-PD-1
SEQ ID NO: 48
RTVAAPSVFIFPPSDEQLKSGTARVGCLLNNFYPREAKVQWKVDNALQSGNSQESVTEQD
SKDSTYSLRSTLTLSKADYEKHKVYACEVTHQGLSSPVTKSFNRGEC (HC of PD-L1 Ab v3.2)
SEQ ID NO: 49
QVQLVQSGAEVKKPGSSVKVSCKASGGTFSSYAISWVRQAPGQGLEWMGGIIPIFGTANY
AQKFQGRVTITADKSTSTAYMELSSLRSEDTAVYYCARSPDYSPYYYYGMDVWGQGTTVT
VSSASTKGPSVFPLAPSSKSTSGGTAALGCLVKDYFPEPVTVSWNSGALTSGVHTFPAVL
QSSGLYSLSSVVTVPSSSLGTQTYICNVNHKPSNTKVDKRVEPKSCDKTHTCPPCPAPEA
AGGPSVFLFPPKPKDTLMISRTPEVTCVVVSVSHEDPEVKFNWYVDGVEVHNAKTKPREE
QYNSTYRVVSVLTVLHQDWLNGKEYKCKVSNKALPAPIEKTISKAKGQPREPQVYVYPPS
RDELTKNQVSLTCLVKGFYPSDIAVEWESNGQPENNYKTTPPVLDSDGSFALVSKLTVDK
SRWQQGNVFSCSVMHEALHNHYTQKSLSLSPGK DNA Sequence of PD-L1 LC (codon variant 1)
SEQ ID NO: 50
CAGTCTGTGC TGACTCAGCC ACCTTCCGCC TCTGGAACCC CAGGACAGAG
GGTCACAATC AGTTGCTCAG GGAGCTCCTC TAACATTGGA AGCAACACTG
TGAATTGGTA CCAGCAGCTG CCTGGGACCG CTCCAAAGCT GCTGATCTAT
GGCAACTCCA ATCGACCATC TGGAGTGCCT GACCGGTTCA GCGGCTCCAA
ATCTGGCACC AGTGCTTCAC TGGCAATTAG TGGCCTGCAG TCCGAGGACG
AAGCCGATTA CTATTGCCAG AGCTACGATA GTTCACTGAG CGGCTCCGTG
TTCGGCGGGG AATCAAGCT GACAGTCCTG GGACAGCCAA AGCGGCGCC
CAGCGTGACT CTGTTTCCAC CCAGCTCCGA GGAACTGCAG GCCAATAAGG
CTACCCTGGT CTGTCTGATT TCCGACTTCT ACCCCGGGGC TGTGACAGTC
GCATGGAAGG CCGATTCTAG TCCTGTGAAA GCAGGAGTCG AGACCACAAC
TCCATCAAAG CAGAGCAACA ACAAGTACGC AGCCGAGAGC GAGCTGTCTC
TGACACCTGA ACAGTGGAAA AGCCACCGGT CTTATAGTTG TCAGGTGACT
CACGAGGGCT CAACAGTGGA AAAGACAGTC GCACCCGCAG AATGCTCA DNA Sequence of PD-L1 HC (codon variant 1)
SEQ ID NO: 51
CAGGTCCAGC TGGTGCAGAG CGGAGCCGAA GTGAAGAAAC CAGGCAGCTC
CGTCAAGGTG TCATGCAAAG CCAGCGGCGG GACTTTCTCT AGTTACGCTA
TCTCCTGGGT GAGACAGGCA CCAGGACAGG GACTGGAGTG GATGGGAGGA
ATCATTCCTA TCTTCGGGAC AGCTAACTAC GCACAGAAGT TTCAGGGAAG
GGTGACTATT ACCGCCGACA AATCTACAAG TACTGCTTAT ATGGAGCTGT
CAAGCCTGAG GAGCGAAGAT ACCGCAGTGT ACTATTGCGC CCGCTCCCCC
GACTACTCTC CTTACTATTA CTATGGCATG ACGTGTGGG GGCAGGGAAC
CACAGTCACA GTGTCCTCTG CCAGCACTAA GGGGCCTTCA GTGTTTCCAC
TGGCACCCAG TTCAAAATCA ACAAGCGGAG GAACTGCCGC TCTGGGATGT
CTGGTGAAGG ACTATTTCCC AGAGCCAGTC ACCGTGAGCT GGAACTCCGG -continued

```
CGCACTGACT TCCGGAGTCC ACACCTTTCC AGCCGTGCTG CAGAGCTCCG

GACTGTACTC TCTGAAGAGT GTGGTCACAG TGCCTTCAAG CTCCCTGGGC

ACCCAGACAT ATATCTGCAA CGTGAATCAC AAGCCTAGTA ATACTAAGGT

TGACAAACGT GTGGAACCAA AGAGCTGTGA TAAAACTCAT ACCTGCCCCC

CTTGTCCGGC GCCAGAGGCA GCAGGAGGAC CAAGCGTGTT CCTGTTTCCA

CCCAAGCCCA AAGACACCCT GATGATTAGC CGAACCCCTG AAGTCACATG

CGTGGTCGTG TCCGTGTCTC ACGAGGACCC AGAAGTCAAG TTCAACTGGT

ACGTGGATGG CGTCGAGGTG CATAATGCCA AGACAAAACC CCGGGAGGAA

CAGTACAACA GCACCTATAG AGTCGTGTCC GTCCTGACAG TGCTGCACCA

GGATTGGCTG AACGGCAAGG AATATAAGTG CAAAGTGTCC AATAAGGCCC

TGCCCGCTCC TATCGAGAAA ACCATTTCTA AGGCAAAAGG CCAGCCTCGC

GAACCACAGG TCTACGTGTA TCCTCCAAGC CGGGACGAGC TGACAAAGAA

CCAGGTCTCC CTGACTTGTC TGGTGAAAGG GTTTTACCCT AGTGATATCG

CTGTGGAGTG GGAATCAAAT GGACAGCCAG AGAACAATTA TAAGACTACC

CCCCCTGTGC TGGACAGTGA TGGGTCATTC GCACTGGTCT CCAAGCTGAC

AGTGGACAAA TCTCGGTGGC AGCAGGGAAA TGTCTTTTCA TGTAGCGTGA

TGCATGAAGC ACTGCACAAC CATTACACCC AGAAGTCACT GTCACTGTCA

CCAGGAAAA
```

---

We claim:

1. An antibody that binds human PD-L1 (SEQ ID NO: 1) and human PD-1 (SEQ ID NO: 2) comprising:
   a) a first heavy chain (HC1) comprising, in order from the N-terminus to the C-terminus, a heavy chain variable region (HCVR) comprising the amino acid sequence of SEQ ID NO: 3, the amino acid sequence of SEQ ID NO: 9 in the CH1 domain, the amino acid sequence of SEQ ID NO: 10 in the CH2 domain, and the amino acid sequence of SEQ ID NO: 11 or SEQ ID NO: 12 in the CH3 domain;
   b) a first light chain (LC1) comprising, in order from the N-terminus to the C-terminus, a light chain variable region (LCVR) comprising the amino acid sequence of SEQ ID NO: 4 and the amino acid sequence of SEQ ID NO: 14 in the constant region;
   c) a second heavy chain (HC2) comprising, in order from the N-terminus to the C-terminus, a HCVR comprising the amino acid sequence of SEQ ID NO: 5, the amino acid sequence of SEQ ID NO: 13 in the CH1 domain, the amino acid sequence of SEQ ID NO: 10 in the CH2 domain, and the amino acid sequence of SEQ ID NO: 12 or the amino acid sequence of SEQ ID NO: 11 in the CH3 domain; and
   d) a second light chain (LC2) comprising, in order from N-terminus, a LCVR comprising the amino acid sequence of SEQ ID NO: 8 and the amino acid sequence of SEQ ID NO: 15 in the constant region, provided that when the amino acid sequence of SEQ ID NO: 11 is present in the CH3 domain of said HC1, the amino acid sequence of SEQ ID NO: 12 is present in the CH3 domain of said HC2; or when the amino acid sequence of SEQ ID NO: 12 is present in the CH3 domain of said HC1, the amino acid sequence of SEQ ID NO: 11 is present in the CH3 domain of said HC2.

2. The antibody of claim 1, wherein said HC1 comprises the amino acid sequence of SEQ ID NO: 11 in the CH3 domain, and wherein said HC2 comprises the HCVR comprising the amino acid sequence of SEQ ID NO: 6 and said HC2 comprises the amino acid sequence of SEQ ID NO: 12 in the CH3 domain.

3. The antibody of claim 1, wherein said HC1, LC1, HC2, and LC2 comprises the amino acid sequences of SEQ ID NO: 49, SEQ ID NO: 30, SEQ ID NO 31, and SEQ ID NO: 34, respectively.

4. The antibody of claim 1, wherein said HC1, LC1, HC2, and LC2 comprises the amino acid sequences of SEQ ID NO: 29, SEQ ID NO: 30, SEQ ID NO: 33, and SEQ ID NO: 34, respectively.

5. A pharmaceutical composition, comprising the antibody of claim 3 and an acceptable carrier, diluent, or excipient.

* * * * *